US006268398B1

(12) United States Patent
Ghosh et al.

(10) Patent No.: US 6,268,398 B1
(45) Date of Patent: Jul. 31, 2001

(54) COMPOUNDS AND METHODS FOR TREATING MITOCHONDRIA-ASSOCIATED DISEASES

(75) Inventors: Soumitra Ghosh; Robert E. Davis, both of San Diego, CA (US)

(73) Assignee: MitoKor, San Diego, CA (US)

(*) Notice: Subject to any disclaimer, the term of this patent is extended or adjusted under 35 U.S.C. 154(b) by 0 days.

(21) Appl. No.: 09/299,044

(22) Filed: Apr. 23, 1999

Related U.S. Application Data

(60) Provisional application No. 60/082,998, filed on Apr. 24, 1998.

(51) Int. Cl.$^7$ ..................... A61K 31/155; A61K 31/135
(52) U.S. Cl. ..................... 514/634; 514/635; 514/646
(58) Field of Search ..................... 514/646, 634, 514/635

(56) References Cited

U.S. PATENT DOCUMENTS

| | | | |
|---|---|---|---|
| 3,541,218 | 11/1970 | Marshall et al. | 424/326 |
| 4,014,934 | * 3/1977 | Hughes et al. | 260/565 |
| 5,614,630 | 3/1997 | Goldin et al. | 546/159 |
| 5,622,968 | 4/1997 | Goldin et al. | 514/313 |
| 5,847,006 | 12/1998 | Magar et al. | 514/634 |

FOREIGN PATENT DOCUMENTS

| | | |
|---|---|---|
| 0 790 240 | 8/1997 | (EP) . |
| WO 93/03714 | 3/1993 | (WO) . |
| WO 96/36325 | 11/1996 | (WO) . |
| WO 97/13504 | 4/1997 | (WO) . |
| WO 97/45108 | 12/1997 | (WO) . |

OTHER PUBLICATIONS

Anderson, "Mitochondrial Dysfunction in Diabetes Mellitus," *Drug Development Research* 46:67–79m 19999.

Beal, "Mitochondrial Dysfunction in Neurodegeneratives Diseases," *Biochimica et Biophysica Acta* 1366:211–223, 1998.

Budd and Nicholls, "A Reevaluation of the Role of Mitochondria in Neuronal Ca$^{2+}$Homeostasis," *J. Neurochem.* 66(1):403–411, 1996.

Dabrowski and Gabryelewicz, "The Effect of Nafamostat Mesilate (FUT–175) and Gabexate Mesilate (FOY) on Multiorgan Oxidant–Antioxidant Balance in Acute Experimental Pancreatitis," *J. Physiology and Pharmacology* 45:455–465, 1994.

Ferner, "Oral Hypoglycemic Agents," *Medical Clinics of North America* 72(6):1323–1335, 1988.

Green and Reed, "Mitochondria and Apoptosis," *Science* 281:1309–1312, 1998.

Hirano and Manabe, "A New Synthetic Protease Inhibitor, E–3123, Prevents Lysosomal and Mitochondrial Fragility in Rat Caerulein–Induced Pancreatitis," *J. International Medical Research* 20:211–217, 1992.

Krentz et al., "Comparative Tolerability Profiles of Oral Antidiabetic Agents," *Drug Safety* 11(4):223–241, 1994.

Li et al., "Amelioration by Cyclosporin A of Brain Damage Following 5 or 10 min of Ischemia in Rats Subjected to Preischemic Hyperglycemia," *Brain Research* 753:133–140, 1997.

Luft, "The Development of Mitochondrial Medicine," *Proc. Natl. Acad. Sci.* USA 91:8731–8738, 1994.

Michel et al., "Effets de Nouveaux Derives Guanydyles et de Diverses Amidinoalkylurees Sur Les Oxydophosphorylations," *Biochemical Pharmacology* 20:2587–2595, 1971.

Santarius et al., "Effects of the Sesquiterpene Lactone Tetraesters Thapsigargicin and Thapsigargin, From Roots of *Thapsia Garganica* L., on Isolated Spinach Chloroplasts," *Toxicon* 25(4):389–399, 1987.

Schäfer, "Biguanides: A Review of History, Pharmacodynamics and Therapy," *Diabete & Metabolisme* 9(2):148–163, 1983.

Schäfer, "Commentary On the Mechanism of Action of Hypoglycemia–Producing Biguanides. A Reevaluation and a Molecular Theory," *Biochem. Pharmac.* 25:2005–2014, 1976.

Schäfer, "Guanidines and Biguanides," *Pharmac. Ther.* 8:275–295, 1980.

Schäfer, "Interaction of Biguanides with Mitochondrial and Synthetic Membranes—The Role of Phospholipids as Natural Binding Sites," *Eur. J. Biochem.* 45:57–66, 1974.

Schäfer and Bojanowski, "Interaction of Biguanides with Mitochondrial and Synthetic Membranes," *Eur. J. Biochem.* 27:364–375, 1972.

(List continued on next page.)

Primary Examiner—Theodore J. Criares
(74) Attorney, Agent, or Firm—Seed Intellectual Property Law Group PLLC

(57) ABSTRACT

Compounds, compositions and methods are disclosed for treating mitochondria-associated diseases, such as cancer, psoriasis, stroke, Alzheimer's Disease and diabetes. The compounds of this invention have structure (I) below, including stereoisomers, prodrugs and pharmaceutically acceptable salts thereof, wherein Ar and L are as defined herein. The methods of this invention are directed to treating a mitochondria-associated disease by administering to a warm-blooded animal in need thereof an effective amount of a compound of structure (I), typically in the form of a pharmaceutical composition.

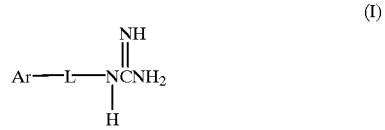

(I)

40 Claims, 1 Drawing Sheet

OTHER PUBLICATIONS

Schäfer and Rieger, "Interaction of Biguanides with Mitochondrial and Synthetic Membranes—Effects of Ion Conductance of Mitochondrial Membranes and Electrical Properties of Phospholipid Bilayers," *Eur. J. Biochem.* 46:613–623, 1974.

Susin et al., "Mitochondria as Regulators of Apoptosis: Doubt No More," *Biochimica et Biophysica Acta* 1366:151–165, 1998.

Swerdlow and Parker, "Mitochondrial Pathology in Parkinson's Disease and Implications for Therapeutic Intervention," *Drug Development Research* 46:44–50, 1999.

Thastrup et al., "Thapsigargin, a Tumor Promoter, Discharges Intracellular $Ca^{2+}$ Stores by Specific Inhibition of the Endoplasmic Reticulum $Ca^{2+}$–ATPase," *Proc. Natl. Acad. Sci. USA* 87:2466–2470, 1990.

White and Reynolds, "Mitochondrial Depolarization in Glutamate–Stimulated Neurons: An Early Signal Specific to Excitotoxin Exposure," *J. Neurosci.* 16(18):5688–6597, 1996.

\* cited by examiner

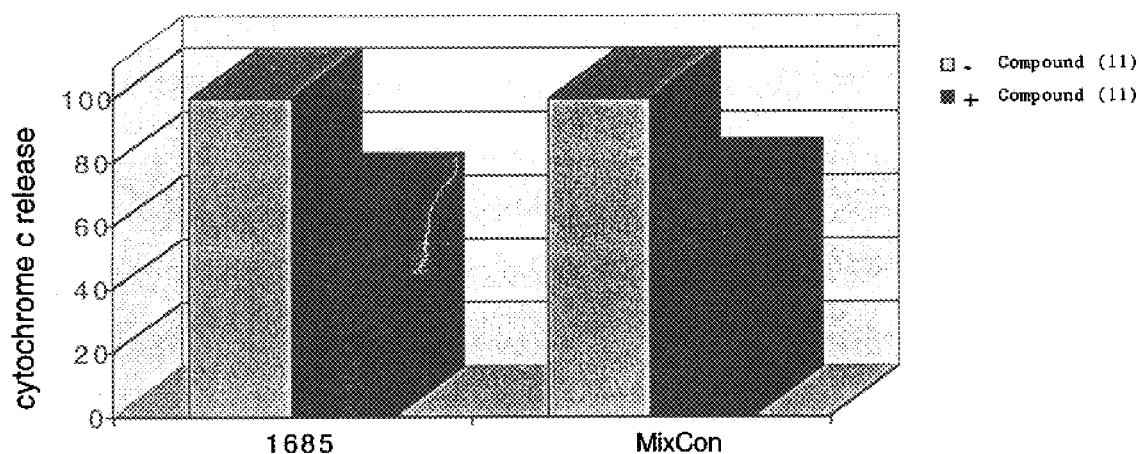
FIGURE

COMPOUNDS AND METHODS FOR TREATING MITOCHONDRIA-ASSOCIATED DISEASES

CROSS-REFERENCE TO RELATED APPLICATION

This application claims the benefit of U.S. Provisional Application No. 60/082,998 filed Apr. 24, 1998.

TECHNICAL FIELD

The present invention relates generally to compounds and methods for treating mitochondria-associated diseases and, more particularly, to (i) diseases and disorders in which free radical mediated oxidative injury leads to tissue degeneration, (ii) diseases and disorders in which cells inappropriately undergo programmed cell death (apoptosis), leading to tissue degeneration, or (iii) diseases and disorders, such as cancer, in which some cells in the body fail to undergo apoptosis with detrimental consequences to the body as a whole. More specifically, the present invention relates to compositions and methods for treating such disease and disorders through the use of compounds which function as, respectively, (1) mitochondria protecting agents, (2) anti-apoptotic agents, or (3) pro-apoptotic agents.

BACKGROUND OF THE INVENTION

Mitochondria are the main energy source in cells of higher organisms, and these organelles provide direct and indirect biochemical regulation of a wide array of cellular respiratory, oxidative and metabolic processes (for a review, see Ernster and Schatz, *J. Cell Biol.* 91:227s–255s, 1981). These include electron transport chain (ETC) activity, which drives oxidative phosphorylation to produce metabolic energy in the form of adenosine triphosphate (ATP), and which also underlies a central mitochondrial role in intracellular calcium homeostasis. In addition to their role in metabolic processes, mitochondria are also involved in the genetically programmed cell suicide sequence known as "apoptosis" (Green and Reed, *Science* 281:1309–1312, 1998; Susin et al., *Biochim. et Biophys. Acta* 1366:151–165, 1998).

Defective mitochondrial activity, including but not limited to failure at any step of the elaborate multi-complex mitochondrial assembly, known as the electron transport chain (ETC), may result in (i) decreases in ATP production, (ii) increases in the generation of highly reactive free radicals (e.g., superoxide, peroxynitrite and hydroxyl radicals, and hydrogen peroxide), (iii) disturbances in intracellular calcium homeostasis and (iv) the release of factors (such as such as cytochrome c and "apoptosis inducing factor") that initiate or stimulate the apoptosis cascade. Because of these biochemical changes, mitochondrial dysfunction has the potential to cause widespread damage to cells and tissues.

A number of diseases and disorders are thought to be caused by or be associated with alterations in mitochondrial metabolism and/or inappropriate induction or suppression of mitochondria-related functions leading to apoptosis. These include, by way of example and not limitation, chronic neurodegenerative disorders such as Alzheimer's disease (AD) and Parkinson's disease (PD); auto-immune diseases; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (leber's; Hereditary; Optic; Neuropathy), Kearns-Sayre disease; Pearson's Syndrome; PEO (Progressive External Ophthalmoplegia); Wolfram syndrome DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis.

According to generally accepted theories of mitochondrial function, proper ETC respiratory activity requires maintenance of an electrochemical potential ($\Delta\psi m$) in the inner mitochondrial membrane by a coupled chemiosmotic mechanism. Conditions that dissipate or collapse this membrane potential, including but not limited to failure at any step of the ETC, may thus prevent ATP biosynthesis and hinder or halt the production of a vital biochemical energy source. Altered or defective mitochondrial activity may also result in a catastrophic mitochondrial collapse that has been termed "mitochondrial permeability transition" (MPT). In addition, mitochondrial proteins such as cytochrome c and "apoptosis inducing factor" may dissociate or be released from mitochondria due to MPT (or the action of mitochondrial proteins such as Bax), and may induce proteases known as caspases and/or stimulate other events in apoptosis (Murphy, *Drug Dev. Res.* 46:18–25, 1999).

Defective mitochondrial activity may alternatively or additionally result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury such as that found in a number of degenerative diseases, and in ischemia (i.e., stroke). (Mitochondrial participation in the apoptotic cascade is believed to also be a key event in the pathogenesis of neuronal death.)

There are, moreover, at least two deleterious consequences of exposure to reactive free radicals arising from mitochondrial dysfunction that adversely impact the mitochondria themselves. First, free radical mediated damage may inactivate one or more of the myriad proteins of the ETC. Second, free radical mediated damage may result in catastrophic mitochondrial collapse that has been termed "transition permeability". According to generally accepted theories of mitochondrial function, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and/or triggering mitochondrial events in the apoptotic cascade. Therefore, by modulating these and other effects of free radical oxidation on mitochondrial structure and function, the present invention provides compositions and methods for protecting mitochondria that are not provided by the mere determination of free radical induced lipid peroxidation.

For example, rapid mitochondrial permeability transition likely entails changes in the inner mitochondrial transmembrane protein adenylate translocase that results in the formation of a "pore". Whether this pore is a distinct conduit or simply a widespread leakiness in the membrane is unresolved. In any event, because permeability transition is potentiated by free radical exposure, it may be more likely to occur in the mitochondria of cells from patients having mitochondria associated diseases that are chronically exposed to such reactive free radicals.

Altered mitochondrial function characteristic of the mitochondria associated diseases may also be related to loss of mitochondrial membrane electrochemical potential by mechanisms other than free radical oxidation, and such transition permeability may result from direct or indirect effects of mitochondrial genes, gene products or related downstream mediator molecules and/or extramitochondrial genes, gene products or related downstream mediators, or from other known or unknown causes. Loss of mitochondrial potential therefore may be a critical event in the progression of mitochondria associated or degenerative diseases.

Diabetes mellitus is a common, degenerative disease affecting 5 to 10 percent of the population in developed countries. The propensity for developing diabetes mellitus is reportedly maternally inherited, suggesting a mitochondrial genetic involvement. (Alcolado, J. C. and Alcolado, R., Br. Med. J. 302:1178–1180 (1991); Reny, S. L., International J. Epidem. 23:886–890 (1994)). Diabetes is a heterogenous disorder with a strong genetic component; monozygotic twins are highly concordant and there is a high incidence of the disease among first degree relatives of affected individuals.

At the cellular level, the degenerative phenotype that may be characteristic of late onset diabetes mellitus includes indicators of altered mitochondrial respiratory function, for example impaired insulin secretion, decreased ATP synthesis and increased levels of reactive oxygen species. Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient non-insulin dependent diabetes (NIDDM) each year. Some of these individuals further progress to insulin dependent diabetes mellitus (IDDM). These forms of diabetes mellitus, NIDDM and IDDM, are associated with decreased release of insulin by pancreatic beta cells and/or a decreased end-organ response to insulin. Other symptoms of diabetes mellitus and conditions that precede or are associated with diabetes mellitus include obesity, vascular pathologies, peripheral and sensory neuropathies, blindness and deafness.

Due to the strong genetic component of diabetes mellitus, the nuclear genome has been the main focus of the search for causative genetic mutations. However, despite intense effort, nuclear genes that segregate with diabetes mellitus are known only for rare mutations in the insulin gene, the insulin receptor gene, the adenosine deaminase gene and the glucokinase gene. Accordingly, mitochondrial defects, which may include but need not be limited to defects related to the discrete non-nuclear mitochondrial genome that resides in mitochondrial DNA, may contribute significantly to the pathogenesis of diabetes mellitus (Anderson, Drug Dev. Res. 46:67–79, 1999).

Parkinson's disease (PD) is a progressive, chronic, mitochondria associated neurodegenerative disorder characterized by the loss and/or atrophy of dopamine-containing neurons in the pars compacta of the suibstantia nigra of the brain. Like Alzheimer's Disease (AD), PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

It has been shown that the neurotoxin 1-methyl-4-phenyl-1,2,3,6-tetrahydropyridine (MPTP) induces parkinsonism in animals and man at least in part through its effects on mitochondria. MPTP is converted to its active metabolite, MPP+, in dopamine neurons; it then becomes concentrated in the mitochondria. The MPP+ then selectively inhibits the mitochondrial enzyme NADH:ubiquinone oxidoreductase ("Complex I"), leading to the increased production of free radicals, reduced production of adenosine triphosphate, and ultimately, the death of affected dopamine neurons.

Mitochondrial Complex I is composed of 40–50 subunits; most are encoded by the nuclear genome and seven by the mitochondrial genome. Since parkinsonism may be induced by exposure to mitochondrial toxins that affect Complex I activity, it appears likely that defects in Complex I proteins may contribute to the pathogenesis of PD by causing a similar biochemical deficiency in Complex I activity. Indeed, defects in mitochondrial Complex I activity have been reported in the blood and brain of PD patients (Parker et al., Am. J. Neurol. 26:719–723, 1989; Swerdlow and Parker, Drug Dev. Res. 46:44–50, 1999).

Similar theories have been advanced for analogous relationships between mitochondrial defects and other neurological diseases, including Alzheimer's disease, Leber's hereditary optic neuropathy, schizophrenia, "mitochondrial encephalopathy, lactic acidosis, and stroke" (MELAS), and "myoclonic epilepsy ragged red fiber syndrome" (MERRF).

For example, Alzheimer's disease (AD) is a chronic, progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

There is evidence that defects in oxidative phosphorylation within the mitochondria are at least a partial cause of sporadic AD. The enzyme cytochrome c oxidase (COX), which makes up part of the mitochondrial electron transport chain (ETC), is present in normal amounts in AD patients; however, the catalytic activity of this enzyme in AD patients and in the brains of AD patients at autopsy has been found to be abnormally low. This suggests that the COX in AD patients is defective, leading to decreased catalytic activity that in some fashion causes or contributes to the symptoms that are characteristic of AD.

One hallmark pathology of AD is the death of selected neuronal populations in discrete regions of the brain. Cell death in AD is presumed to be apoptotic because signs of programmed cell death (PCD) are seen and indicators of active gliosis and necrosis are not found (Smale et al., Exp. Neurolog. 133:225–230, 1995; Cotman et al., Molec. Neitrobiol. 10:19–45, 1995.) The consequences of cell death in AD, neuronal and synaptic loss, are closely associated with the clinical diagnosis of AD and are highly correlated with the degree of dementia in AD (DeKosky et al., *Ann. Neurology* 2757–464, 1990).

Mitochondrial dysfunction is thought to be critical in the cascade of events leading to apoptosis in various cell types (Kroemer et al., *FASEB J*. 9:1277–1287, 1995), and may be a cause of apoptotic cell death in neurons of the AD brain. Altered mitochondrial physiology may be among the earliest events in PCD (Zamzami et al., *J. Exp. Med*. 182:367–77, 1995; Zamzami et al., *J. Exp. Med*. 181:1661–72, 1995) and elevated reactive oxygen species (ROS) levels that result from such altered mitochondrial function may initiate the apoptotic cascade (Ausserer et al., *Mol. Cell. Biol*. 14:5032–42, 1994). In several cell types, including neurons, reduction in the mitochondrial membrane potential ($\Delta\psi m$) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Perturbation of mitochondrial respiratory activity leading to altered cellular metabolic states, such as elevated intracellular ROS, may occur in mitochondria associated diseases and may further induce pathogenetic events via apoptotic mechanisms.

Oxidatively stressed mitochondria may release a preformed soluble factor that can induce chromosomal condensation, an event preceding apoptosis (Marchetti et al., *Cancer Res*. 56:2033–38, 1996). In addition, members of the Bcl-2 family of anti-apoptosis gene products are located within the outer mitochondrial membrane (Monaghan et al., *J. Histochem. Cytochem*. 40:1819–25, 1992) and these proteins appear to protect membranes from oxidative stress (Korsmeyer et al, *Biochim. Biophys. Act*. 1271:63, 1995). Localization of Bcl-2 to this membrane appears to be indispensable for modulation of apoptosis (Nguyen et al., *J. Biol. Chem*. 269:16521–24, 1994). Thus, changes in mitochondrial physiology may be important mediators of apoptosis. To the extent that apoptotic cell death is a prominent feature of neuronal loss in AD. mitochondrial dysfunction may be critical to the progression of this disease and may also be a contributing factor in other mitochondria associated diseases.

Focal defects in energy metabolism in the mitochondria, with accompanying increases in oxidative stress, may be associated with AD. It is well-established that energy metabolism is impaired in AD brain (Palmer et al., *Brain Res*. 645:338–42, 1994; Pappolla et al., *Am. J. Pathol*. 140:621–28, 1992; Jeandel et al., *Gerontol*. 35:275, 1989; Balazs et al., *Neurochem. Res*. 19:1131–37, 1994; Mecocci et al., *Ann. Neurol*. 36:747–751, 1994; Gsell et al., *J. Neurochem*. 64:1216–23, 1995). For example, regionally specific deficits in energy metabolism in AD brains have been reported in a number of positron emission tomography studies (Kuhl, et al., *J. Cereb. Blood Flow Metab*. 7:S406, 1987; Grady, et al., *J. Clin. Exp. Neuropsychol*. 10:576–96, 1988; Haxby et al., *Arch. Neurol*. 47:753–60, 1990; Azari et al., *J. Cereb. Blood Flow Metab*. 13:438–47, 1993). Metabolic defects in the temporoparietal neocortex of AD patients apparently presage cognitive decline by several years. Skin fibroblasts from AD patients display decreased glucose utilization and increased oxidation of glucose, leading to the formation of glycosylation end products (Yan et al., *Proc. Nat. Acad. Sci. U.S.A*. 91:7787–91, 1994). Cortical tissue from postmortem AD brain shows decreased activity of the mitochondrial enzymes pyruvate dehydrooenase (Sheu et al., *Ann. Neurol*. 17:444–49, 1985) and α-ketoglutarate dehydrogenase (Mastrogiacomo et al., *J. Neurochem*. 6:2007–2014, 1994), which are both key enzymes in energy metabolism. Functional magnetic resonance spectroscopy studies have shown increased levels of inorganic phosphate relative to phosphocreatine in AD brain, suggesting an accumulation of precursors that arises from decreased ATP production by mitochondria (Pettegrew et al., *Neurobiol. of Aging* 15:117–32, 1994; Pettigrew et al., *Neurobiol. of Aging* 16:973–75, 1995). In addition, the levels of pyruvate, but not of glucose or lactate, are reported to be increased in the cerebrospinal fluid of AD patients, consistent with defects in cerebral mitochondrial electron transport chain (ETC) activity (Pametti etal., *Neurosci. Lett*. 199:231–33, 1995).

Signs of oxidative injury are prominent features of AD pathology and, as noted above, reactive oxygen species (ROS) are critical mediators of neuronal degeneration. Indeed, studies at autopsy show that markers of protein, DNA and lipid peroxidation are increased in AD brain (Palmer et al., *Brain Res*. 645:338–42, 1994; Pappolla et al., *Am. J. Pathol*. 140:621–28, 1992; Jeandel et al., *Gerontol*. 35:275–82, 1989; Balazs et al., *Arch. Neurol*. 4:864, 1994; Mecocci et al., *Ann. Neurol*. 36:747–751. 1994; Smith et al., *Proc. Nat. Acad. Sci. U.S.A*. 88:10540–10543, 1991). In hippocampal tissue from AD but not from controls, carbonyl formation indicative of protein oxidation is increased in neuronal cytoplasm, and nuclei of neurons and glia (Smith et al., *Nature* 382:120–21, 1996). Neurofibrillary tangles also appear to be prominent sites of protein oxidation (Schweers et al., *Proc. Nat. Acad. Sci. U.S.A*. 92:8463, 1995; Blass et al., *Arch. Neurol*. 4:864, 1990). Under stressed and non-stressed conditions incubation of cortical tissue from AD brains taken at autopsy demonstrate increased free radical production relative to non-AD controls. In addition, the activities of critical antioxidant enzymes, particularly catalase. are reduced in AD (Gsell et al., *J. Neurochem*. 64:1216–23, 1995), suggesting that the AD brain is vulnerable to increased ROS production. Thus, oxidative stress may contribute significantly to the pathology of mitochondria associated diseases such as AD, where mitochondrial dysfunction and/or elevated ROS may be present.

Increasing evidence points to the fundamental role of mitochondrial dysfunction in chronic neurodegenerative diseases (Beal, *Biochim. Biophys. Acta* 1366: 211–223, 1998), and recent studies implicate mitochondria for regulating the events that lead to necrotic and apoptotic cell death (Susin et al., *Biochim. Biophys. Acta* 1366: 151–168, 1998). Stressed (by, e.g., free radicals, high intracellular calcium, loss of ATP, among others) mitochondria may release preformed soluble factors that can initiate apoptosis through an interaction with apoptosomes (Marchetti et al., *Cancer Res*. 56:2033–38, 1996; Li et al., *Cell* 91: 479–89, 1997). Release of preformed soluble factors by stressed mitochondria, like cytochrome c, may occur as a consequence of a number of events. In any event, it is thought that the magnitude of stress (ROS, intracellular calcium levels, etc.) influences the changes in mitochondrial physiology that ultimately determine whether cell death occurs via a necrotic or apoptotic pathway. To the extent that apoptotic cell death is a prominent feature of degenerative diseases, mitochondrial dysfunction may be a critical factor in disease progression.

In contrast to chronic neurodegenerative diseases, neuronal death following stroke occurs in an acute manner. A vast amount of literature now documents the importance of mitochondrial function in neuronal death following ischemia/reperfusion injury that accompanies stroke, cardiac arrest and traumatic injury to the brain. Experimental support continues to accumulate for a central role of defective energy metabolism, alteration in mitochondrial function leading to increased oxygen radical production and impaired intracellular calcium homeostasis, and active mitochondrial participation in the apoptotic cascade in the pathogenesis of acute neurodegeneration.

A stroke occurs when a region of the brain loses perfuision and neurons die acutely or in a delayed manner as a result of this sudden ischemic event. Upon cessation of the blood supply to the brain, tissue ATP concentration drops to negligible levels within minutes. At the core of the infarct, lack of mitochondrial ATP production causes loss of ionic homeostasis, leading to osmotic cell lysis and necrotic death. A number of secondary changes can also contribute to cell death following the drop in mitochondrial ATP. Cell death in acute neuronal injury radiates from the center of an infarct where neurons die primarily by necrosis to the penumbra where neurons undergo apoptosis to the periphery where the tissue is still undamaged (Martin et al., *Brain Res. Bull.* 46:281–309, 1998).

Much of the injury to neurons in the penumbra is caused by excitotoxicity induced by glutamate released during cell lysis at the infarct focus, especially when exacerbated by bioenergetic failure of the mitochondria from oxygen deprivation (MacManus and Linnik, *J. Cerehral Blood Flow Metab.* 17:815–832, 1997). The initial trigger in excitotoxicity is the massive influx of $Ca^{2+}$ primarily through the NMDA receptors, resulting in increased uptake of $Ca^{2+}$ into the mitochondria (reviewed by Dykens, "Free radicals and mitochondrial dysfunction in excitotoxicity and neurodegenerative diseases" in *Cell Death and Diseases of the Nervous System*, V. E. Koliatos and R. R. Ratan, eds., Humana Press, New Jersey, pages 45–68, 1999). The $Ca^{2+}$ overload collapses the mitochondrial membrane potential ($\Delta\psi m$) and induces increased production of reactive oxygen species (Dykens. *J Neurochem* 63:584–591, 1994; Dykens, "Mitochondrial radical production and mechanisms of oxidative excitotoxicity" in *The Oxygen Paradox*, K. J. A. Davies, and F. Ursini, eds., Cleup Press, U. of Padova. pages 453–467, 1995). If severe enough, $\Delta\psi_n$ collapse and mitochondrial $Ca^{2+}$ sequestration can induce opening of a pore in the inner mitochondrial membrane through a process called mitochondrial permeability transition (MPT). indirectly releasing cytochrome c and other proteins that initiate apoptosis (Bernardi et al., *J. Biol Chem* 267:2934–2939, 1994; Zoratti and Szabo, *Biochim Biophys Acta* 1241:139–176, 1995; Ellerby et al., *J Neurosci* 17:6165–6178, 1997). Consistent with these observations, glutamate-induced excitotoxicity can be inhibited by preventing mitochondrial $Ca^{2+}$ uptake or blockino MPT (Budd and Nichols, *J Neurochem* 66:403–411, 1996; White and Reynolds, *J Neurosci* 16:5688–5697, 1996; Li et al., *Brain Res* 753:133–140, 1997).

Whereas mitochondria-mediated apoptosis may be critical in degenerative diseases, it is thought that disorders such as cancer involve the unregulated and undesirable growth (hyperproliferation) of cells that have somehow escaped a mechanism that normally triggers apoptosis in such undesirable cells. Enhanced expression of the anti-apoptotic protein, Bcl-2 and its homologues is involved in the pathogenesis of numerous human cancers. Bcl-2 acts by inhibiting programmed cell death and overexpression of Bcl-2. and the related protein Bcl-xL. block mitochondrial release of cytochrome c from mitochondria and the activation of caspase 3 (Yang et al, *Science* 275:1129–1132, 1997; Kluck et al., *Science* 275:1132–1136, 1997; Kharbanda et al., *Proc. Natl. Acad. Sci. U.S.A.* 94:6939–6942, 1997). In contrast, overexpression of Bcl-2 and Bcl-xL protect against the mitochondrial dysfunction preceding nuclear apoptosis that is induced by chemotherapeutic agents. In addition, acquired multi-drug resistance to cytotoxic drugs is associated with inhibition cytochrome c release that is dependent on overexpression of Bcl-xL (Kojima et al., *J. Biol. Chem.* 273: 16647–16650, 1998). Because mitochondria have been implicated in apoptosis, it is expected that agents that interact with mitochondrial components will effect a cell's capacity to undergo apoptosis. Thus, agents that induce or promote apoptosis in hyperproliferative cells are expected to be useful in treating hyperproliferative disorders and diseases such as cancer.

Thus, alteration of mitochondrial function has great potential for a broadbased therapeutic strategy for designing drugs to treat degenerative disorders and diseases as well as hyperproliferative diseases. Depending on the disease or disorder for which treatment is sought, such drugs may be mitochondria protecting agents, antiapoptotic agents or pro-apoptotic agents.

Clearly there is a need for compounds and methods that limit or prevent damage to organelles, cells and tissues by free radicals generated intracellularly as a direct or indirect result of mitochondrial dysfunction. In particular, because mitochondria are essential organelles for producing metabolic energy, agents that protect mitochondria against oxidative injury by free radicals would be especially useful. Such agents may be suitable for the treatment of degenerative diseases including mitochondria associated diseases. Existing approaches to identifying agents that limit oxidative damage may not include determination of whether such agents may help protect mitochondrial structure and/or function.

There is also a need for compounds and methods that limit or prevent damage to cells and tissues that occurs directly or indirectly as a result of necrosis and/or inappropriate apoptosis. In particular, because mitochondria are mediators of apoptotic events, agents that modulate mitochondrially mediated pro-apoptotic events would be especially useful. Such agents may be suitable for the treatment of acute degenerative events such as stroke. Given the limited therapeutic window for blockade of necrotic death at the core of an infarct, it may be particularly desirable to develop therapeutic strategies to limit neuronal death by preventing mitochondrial dysfunction in the non-necrotic regions of an infarct. Agents and methods that maintain mitochondrial integrity during transient ischemia and the ensuing wave of excitotoxicity would be expected to be novel neuroprotective agents with utility in limiting strokerelated neuronal injury.

There is also a need for compounds and methods that inhibit the growth or enhance the death of cells and tissues that have escaped appropriate apoptotic signals, as well as cytotoxic agents that cause the death of undesirable (e.g., cancer) cells by triggering the apoptotic cascade. In particular. because mitochondria are mediators of apoptotic events, agents that stimulate mitochondrially mediated pro-apoptotic events would be especially useful. Such agents may be suitable for the treatment of hyperproliferative diseases such as cancer and psoriasis.

The present invention fulfills these needs and provides other related advantages. Those skilled in the art will recognize further advantages and benefits of the invention after reading the disclosure.

SUMMARY OF THE INVENTION

Briefly stated, the present invention is directed to the treatment of mitochondria-associated diseases by administration to a warm-blooded animal in need thereof an effective amount of a compound having the following general structure (I):

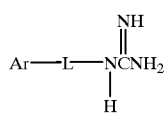 (I)

where Ar is phenyl or naphthyl optionally substituted with 1 to 5 $R_2$ groups and L is an optional linker moiety.

In one embodiment, Ar is phenyl, naphthyl, 4-bromonaphthyl, 3,5-di-t-butyl-4-hydroxyphenyl, 2-methoxy-4-carboxylphenyl, 2-chloro-4-carboxyl-5-methoxyphenyl 3,5-di-tetrafluoromethylphenyl, 3,5-difluorophenyl, 3,4,5-trimethoxyphenyl, 4-n-hexoxyphenyl, 4-fluorophenyl, 3-tri fluorophenyl, 2-carbinolphenyl, 2-chloro-5-methylphenyl, 3-carboxylphenyl, 3-carboxyl-4-hydroxyphenyl, 2-methyl-4-carboxylphenyl, 4-methoxyphenyl, 2-hydroxyphenyl, 4-(N-morphinol) phenyl, 3,4-dihydroxyphenyl, 2,4-dimethylphenyl, 2-methyl-4-hydroxyphenyl, 4-n-octylphenyl, 2-hydroxy-5-n-octylphenyl, 4-chlorophenyl, or 2-methyl-4-chlorophenyl.

In another embodiment the optional linker moiety L is not present, while in a further embodiment L is present and is —$CH_2NH$—, —$CH_2CH_2$—, —$CH(OH)CH_2$—, —$CH_2N(CH_3)$— or —$NHC(=NH)$—.

In still further embodiments, methods are disclosed for treating mitochondria-associated diseases by administering one or more compounds of structure (I) in the form of a pharmaceutical composition. Thus, pharmaceutical compositions are also disclosed comprising a compound of structure (I) in combination with a pharmaceutically acceptable carrier or diluent.

In the context of this invention, mitochondria-associated disease include diseases in which free radical mediated oxidative injury leads to tissue degeneration. diseases in which cells inappropriately undergo apoptosis, and diseases in which cells fail to undergo apoptosis. Thus. the methods of this invention include the treatment of a wide number of mitochondria-associated diseases. including (but not limited to Alzheimer's Disease, Parkinson's Disease, Huntington's Disease, auto-immune disease, diabetes mellitus (Type I or Type II), congenital muscular dystrophy, fatal infantile myopathy, "later-onset" myopathy, MELAS (mitochondrial encephalopathy, lactic acidosis, and stroke), MIDD (mitochondrial diabetes and deafness), MERFF (myoclonic epilepsy ragged red fiber syndrome), arthritis, NARP (Neuropathy; Ataxia; Retinitis Pigmentosa), MNGIE (Myopathy and external ophthalmoplegia; Neuropathy; Gastro-Intestinal; Encephalopathy), LNION (Leber's; Hereditary; Optic; Neuropathy), Kearns-Sayre disease, Pearson's Syndrome, PEO (Progressive External Ophthalmoplegia), Wolfram syndrome, DIDMOAD (Diabetes Insipidus, Diabetes Mellitus, Optic Atrophy, Deafness), Leigh's Syndrome, dystonia, schizophrenia, cancer and psoriasis.

These and other aspects of the present invention will become evident upon reference to the following detailed description and attached drawings. In addition, various references are set forth herein which describe in more detail certain aspects of this invention, and are therefore incorporated by reference in their entirety.

BRIEF DESCRIPTION OF THE DRAWING

The attached FIGURE depicts attenuation of apoptosis in cells treated with a representative compound of this invention, compound (11), prior to induction of an apoptotic pathway with ionophore.

DETAILED DESCRIPTION OF THE INVENTION

The present invention is directed generally to compounds useful as mitochondria protecting agents, as well as methods useful for treating mitochondria associated diseases. More specifically, the mitochondria protecting agents of this invention have the following structure (I):

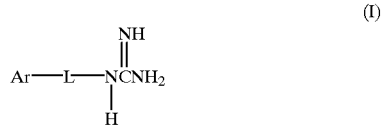 (I)

including stereoisomers, prodrugs and pharmaceutically acceptable salts thereof,
wherein:
Ar is phenyl or naphthyl optionally substituted with 1 to 5 $R_2$ groups;
L is an optional linker moiety selected from —$(CH_2)_n$—, —$(CH_2)_nNH$—, —$(CH_2)_nN(C_{1-4}alkyl)$—, —$NHC(=NH)$— and —$(CH_2)_nO(CH_2)_n$—, wherein n is 1–4 and each linker moiety is optionally substituted with 1 to 5 $R_3$ groups;
$R_2$ is hydroxy, $C_{1-2}$alkyl, $C_{1-12}$alkyloxy, halo, —$NH_2$, —NHR, —NRR, cyano, nitro, —SR, —COOH, $C_{7-12}$aralkyl or heterocycle; or $C_{1-12}$alkyl, $C_{1-2}$alkyloxy, —$NH_2$, —NHR, —NRR, —SR, $C_{7-12}$aralkyl or heterocycle substituted with 1 to 5 $R_3$ groups;
$R_3$ is hydroxy, halo, $C_{1-4}$alkyl, —OR, —$NH_2$, —NHR or —NRR; and
each occurrence of R is independently selected from $C_{1-4}$alkyl.

As used herein, a "$C_{1-4}$ alkyl" is a straight chain or branched, saturated or unsaturated hydrocarbon moiety having from 1 to 4 carbon atoms, such as methyl, ethyl, n-propyl, isopropyl, n-butyl, t-butyl, and the like. Similarly, "$C_{1-12}$alkyl" is a straight chain or branched, saturated or unsaturated hydrocarbon moiety having from 1 to 12 carbon atoms, including the above $C_{1-4}$alkyls as well as n-pentyl, n-octyl and the like, and branched hydrocarbons such as 1,1-dimethyl-3,3-dimethyl-butyl and the like.

"$C_{1-12}$alkyloxy" means —O— $C_{1-12}$alkyl, such as methoxy, ethoxy and the like.

"Halo" means fluoro, chloro, bromo or iodo.

"$C_{7-12}$aralkyl" refers to a moiety having both an aryl and alkyl portion, wherein the combined numbers of carbon atoms for both portions range from 7 to 12. As used herein, "aryl" refers to aromatic monocyclic and fused, homoaryl and heteroaryl groups. "Homoaryl" refers to an aromatic compound having an aromatic ring made up of only carbon atoms, while the term "heteroaryl" refers to an aromatic compound having an aromatic ring which contains, in addition to carbon, one or more other atoms, most commonly nitrogen, oxygen and sulfur. The term "monocyclic aryl" refers to an aromatic compound having a single aromatic ring, while "fused aryl" refers to aromatic rings that shares a pair of carbon atoms, and includes multiple fused rings. Representative $C_{7-12}$aralkyl moieties include, but are not limited to, benzyl and —$C(CH_3)_2$-phenyl.

"Heterocycle" means a 5- to 7-membered monocyclic or 7- to 10-membered bicyclic heterocycle ring which is either saturated or unsaturated, and which contains carbon atoms and from 1 to 4 heteroatoms selected from N, O and S, wherein the N and S heteroatoms may be optionally oxidized, and wherein the N heteroatom may be optionally quaternized. The heterocycle may be attached via any carbon atom or heteroatom on the ring. Representative heterocycles include, for example, morpholine.

The phrase "substituted $C_{1-12}$alkyl, $C_{1-12}$alkyloxy, —$NH_2$, —NHR, —NRR, —SR, $C_{7-12}$aralkyl or heterocycle substituted with 1 to 5 $R_3$ groups" means that from one o five hydrogen atoms of the $C_{1-12}$alkyl, $C_{1-11}$alkyloxy —$NH_2$, —NHR, —NRR, —SR, $C_{7-12}$aralkyl or heterocycle moiety have been replaced with a R, group, wherein each $R_3$ group may be the same or different. For example, representative substituted $C_{1-12}$alkyls include trifluromethyl and —$CH_2OH$.

Similarly, a "substituted" linker moiety is when from one to five hydrogen atoms of —$(CH_2)_n$—, —$(CH_2)_nNH$—, —$(CH_2)_nN(C_{1-4}$alkyl)—, —NHC(=NH)— or —$(CH_2)_nO(CH_2)_n$— have been replaced with a $R_3$ group, wherein each $R_3$ group may be me or different. For example, representative substituted linkers include —CH(OH)$CH_2$— when the linker is —$CH_2CH_2$— substituted with a hydroxyl $R_3$ group.

Representative compounds of this invention and analytical data for the me are presented in the following Tables 1 and 2.

TABLE 1

Representative Compounds

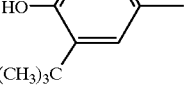

| Cpd. | Ar | L |
|---|---|---|
| (1) | 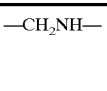 | —$CH_2NH$— |
| (2) | 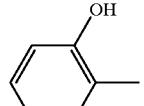 | —$(CH_2)_2$— |
| (3) | 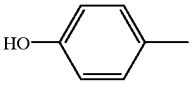 | (none) |
| (4) | 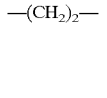 | 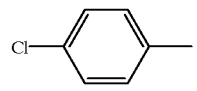 |

TABLE 1-continued

Representative Compounds

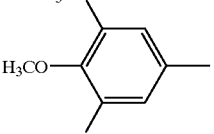

| Cpd. | Ar | L |
|---|---|---|
| (5) | 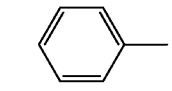 | —$(CH_2)_2$— |
| (6) | 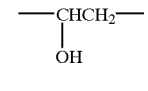 | (none) |
| (7) | 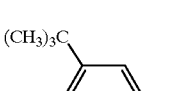 | (none) |
| (8) | 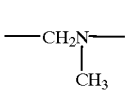 | (none) |
| (9) | 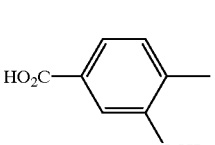 | (none) |
| (10) | 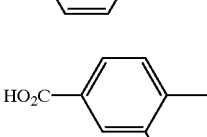 | —CHCH$_2$—<br>    \|<br>    OH |
| (11) | 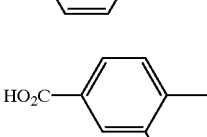 | —NHC(=NH)— |
| (12) | 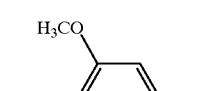 | (none) |
| (13) | 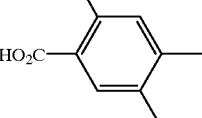 | (none) |

TABLE 1-continued

Representative Compounds

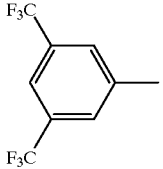

| Cpd. | Ar | L |
|---|---|---|
| (14) | 3,5-bis(trifluoromethyl)phenyl | (none) |
| (15) | 3,5-difluorophenyl | (none) |
| (16) | 4-(pentyloxy)phenyl (CH₃(CH₂)₅O—C₆H₄—) | (none) |
| (17) | 4-fluorophenyl | (none) |
| (18) | 3-(trifluoromethyl)phenyl | (none) |
| (19) | 2-(hydroxymethyl)phenyl | (none) |
| (20) | phenyl | (none) |
| (21) | 4-chloro-3-methylphenyl | (none) |
| (22) | 3-carboxyphenyl | (none) |
| (23) | 2-hydroxy-5-methyl-3-carboxyphenyl | (none) |
| (24) | 3-methyl-4-carboxyphenyl | (none) |
| (25) | 4-methoxyphenyl | —CH₂NH— |
| (26) | 2-hydroxyphenyl | —CH₂NH— |
| (27) | 4-morpholinophenyl | (none) |
| (28) | 3,4-dihydroxyphenyl | —CH₂CH₂— |
| (29) | 2,4-dimethylphenyl | (none) |
| (30) | 3-methyl-4-hydroxyphenyl | (none) |
| (31) | 4-octylphenyl (CH₃(CH₂)₇—C₆H₄—) | (none) |
| (32) | 3-chloro-2-methylphenyl | (none) |

TABLE 1-continued

Representative Compounds

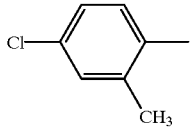

| Cpd. | Ar | L |
|---|---|---|
| (33) | 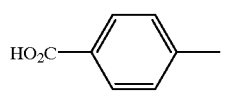 | (none) |
| (34) | 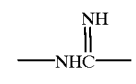 | $-\text{NHC}(=\text{NH})-$ |
| (35) | 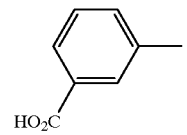 | $-\text{NHC}(=\text{NH})-$ |

TABLE 2

Analytical Data

| Cpd. | $^1$H NMR (500 MHz) | MW\ |
|---|---|---|
| (1) | (acetate salt in CD$_3$OD): δ 7.14(s, 2H), 3.82(s, 2H), 1.97(acetate CH$_3$ peak), 1.42(s, 18H) | 352 293.2(GH)$^+$ |
| (2) | (acetate salt in CD$_3$OD): δ 7.07(d, 2H, J = 8.4 Hz), 6.74(d, 2H, J = 8.4 Hz), 3.39 (t, 2H, J = 7Hz), 2.78(t, 2H, J = 7Hz), 1.97(acetate CH$_3$ peak). | 235 223.2(GH)$^+$ |
| (3) | (in CD$_3$OD): δ 6.59(s, 2H), 3.84(s, 6H), 3.77(s, 3H) | 225 226(GH)$^+$ |
| (4) | (in CD$_3$OD): δ 7.11(s, 2H), 3.87(d, 1H), 3.58(d, 1H), 2.68(s, 3H), 1.41(s, 18H) | 306 308.2(GH$_2$)$^+$ |
| (5) | (acetate salt in CD$_3$OD): δ 6.89(d, 1H, J = 8.1Hz), 6.87(d, 1H, 1.9Hz),(dd, 1H, J = 8.1, 1.9), 3.83(s, 3H), 3.80(s, 3H), 3.43(t, 2H, J = 7.1Hz), 2.82(t, 2H, J = 7.1Hz), 1.97(acetate CH$_3$ peak). | 283 179.2(GH)$^+$ |
| (6) | (in CD$_3$OD): δ 7.04(dd, 1H, J = 2.1, 8.3 Hz), 6.98(d, 1H, J = 2.1Hz), 6.87(d, 1H, J = 8.3Hz), 2.54(t, 2H, 7.6Hz), 1.58(br. t, 2H, 7.6Hz), 1.30(m, 10 H), 0.89(t, 3H, J = 7Hz). | 263 264.1(GH)$^+$ |
| (7) | (acetate salt in CD$_3$OD): δ 7.93(dd, 1H, J = 6.6, 2.1Hz), 8.01(m, 1H), 7.92(d, 1H, J = 8Hz), 7.74(m, 2H), 7.43(d, 7.7 Hz), 1.98(acetate CH$_3$ peak) | 323 263.9(G)$^+$ |
| (9) | (acetate salt in CD$_3$OD): δ 7.47(d, 2H, J = 8.6Hz), 7.27(d, 2H, J = 8.6Hz), 1.95 (acetate CH$_3$ peak) | 229 170.1(GH)$^+$ |
| (10) | (in CD$_3$OD): δ 7.42(d, 2H), 7.37(m, 2H), 7.30(m, 1H), 4.83(m, 1H), 3.43 (dd, 1H, J = 13.7, 3.7Hz) 3.35(dd, 1H, 13.9, 7.5Hz) | 179 179.9(G)$^+$ |
| (11) | (HCl salt in CD$_3$OD): δ 7.33(d, 4H), 7.14(m, 1H) | 213.5 177.8(GH)$^+$ |
| (12) | (acetate salt in CD$_3$OD): δ 8.15(d, 1H, J = 8.2Hz), 7.49(d, 1H, J = 1.6Hz), 7.46 (dd, 1H, J = 8.2, 1.6Hz), 3.95(s, 3H), 1.93(acetate CH$_3$ peak) | 269 208.0(G–H)$^+$ |
| (13) | (in CD$_3$OD): δ 8.18(s, 1H), 7.97(s, 1H), 3.97(s, 3H) | 243 244.2(GH)$^+$ |
| (14) | (acetate salt in CD$_3$OD): δ 7.92(s, 1H), 7.89(s, 2H), 1.97(acetate CH$_3$ peak) | 331 271.9(GH)$^+$ |
| (15) | (in CD$_3$OD): δ 6.94(d, 1H), 6.93(d, 2H) | 171 172(GH)$^+$ |
| (16) | (acetate salt in CD$_3$OD): δ 7.18(d, 2H, J = 8.8Hz), 6.99(d, 2H, J = 8.8Hz), 3.99 (t, 2H, J = 6.5Hz), 1.98(acetate CH$_3$ peak), 1.77(m, 2H), 1.47(m, 2H), 1.36 (m, 4H), 0.92(t, 3H, 6.8Hz) | 295 236.0(GH)$^+$ |
| (17) | (acetate salt in CD$_3$OD): δ 7.31(m, 2H), 7.20(m, 2H) 1.97(acetate CH$_3$ peak) | 213 154.0(GH)$^+$ |
| (18) | (acetate salt in CD$_3$OD): δ 7.55–7.68(m, 4H), 1.96(acetate CH$_3$ peak) | 263 204.0(GH)$^+$ |
| (19) | (acetate salt in CD$_3$OD): δ 7.55(m, 1H), 7.41(m, 2H), 7.30(m, 2H), 4.63(s, 2H), 1.98(acetate CH$_3$ peak) | 225 166.0(GH)$^+$ |
| (20) | (in CD$_3$OD): δ 7.47(m, 1H), 7.36(m, 2H), 7.29(m, 2H) | 135 136.1(GH)$^+$ |
| (21) | (acetate salt in CD$_3$OD): δ 7.45(d, 1H, J = 8.1Hz), 7.24(m, 2H), 2.36(s, 3H), 1.95(acetate CH$_3$ peak) | 243 184(GH)$^+$ |
| (22) | (in CD$_3$OD): δ 7.84(m, 1H), 7.55(dd, 1H, J = 8.1, 2.1Hz), 7.46(m, 1H), 7.34 (m, 1H) | 179 202.2(G + Na)$^+$ |
| (23) | (acetate salt in CD$_3$OD): δ 7.76(d, 1H, J = 2.6Hz), 7.37(dd, 1H, 8.8, 2.6Hz), 7.02(d, 1H, 8.8Hz), 1.99(acetate CH$_3$ peak) | 255 196(GH)$^+$ |
| (24) | (in CD$_3$OD): δ 7.84(d, 1H, J = 8.5Hz), 7.07(br. S, 1H), 7.66(dd, 1H J 8.5, 2.1Hz), 2.30(3H) | 193 216.2(G + Na)$^+$ |
| (25) | (acetate salt in CD$_3$OD): δ 7.28(d, 2H, J 8.6Hz), 6.89(d, 2H, J = 8.6Hz), 3.85 (s, 2H), 3.77(s, 3H), 1.93(acetate CH$_3$ peak) | 254 195.3(GH)$^+$ |
| (26) | (acetate salt in CD$_3$OD): δ 7.16(m, 2H), 6.79(m, 2H), 3.93(s, 2H), 1.93(acetate CH$_3$ peak) | 240 181.2(GH)$^+$ |
| (27) | (acetate salt in CD$_3$OD): δ 7.16(d, 2H, J 9Hz), 7.05(d, 2H, J = 9Hz), 3.83(m, 4H), 3.18(m, 2H), 1.98(acetate CH$_3$ peak) | 280 221.2(GH)$^+$ |
| (28) | (acetate salt in CD$_3$OD): δ 6.7(d, 1H, J = 8Hz), 6.66(d, 1H, 1.9Hz), 6.55(dd, 1H, J = 8, 1.9Hz), 3.37(t, 2H, J = 7Hz),, 2.72(t, 2H, J = 7Hz), 1.99(acetate CH$_3$ peak) | 255 196.1(GH)$^+$ |
| (29) | (acetate salt in CD$_3$OD): δ 7.18(br. S, 1H), 7.10(br. T, 2H), 2.33(s, 3H), 2.25 (s., 3H), 1.98(acetate CH$_3$ peak) | 223 164.2(GH)$^+$ |
| (30) | (acetate salt in CD$_3$OD): δ 7.03(d, 1H, J = 8.5Hz), 6.76(d, 1H, J = 2.7Hz), 6.69 (dd, 1H, J = 8.5, 2.7Hz), 2.20(s, 3H), 1.98(acetate CH$_3$ peak) | 225 166.3(GH)$^+$ |
| (31) | (in CD$_3$OD): δ 7.29(br. d, 2H, J = 8.2 Hz), 7.17(dd, 2H, J = 6.7, 1.8Hz), 2.64 (t, 2H, J = 7.6Hz), 1.62(m, 2H), 1.30 (m, 10H), 0.89(t, 3H, J = 6.7Hz) | 247 248.4(GH)$^+$ |
| (32) | (acetate salt in CD$_3$OD): δ 7.48(dd, 1H, J = 8.0, 1.0Hz), 7.29(t, 1H), 7.21(br. d, 1H), 2.40(s, 3H), 1.93(acetate CH$_3$ peak) | 243 183.9(GH)$^+$ |
| (33) | (acetate salt in CD$_3$OD): δ 7.39(d, 1H, 2.2Hz), 7.30(dd, 1H, J = 8.6, 2.2Hz), 7.22(d, 1H, 8.3Hz), 2.28(s, 3H), 1.98 (acetate CH$_3$ peak) | 243 183.9(GH)$^+$ |
| (34) | (in CD$_3$OD): δ 7.97(d, 2H), 7.49(d, 2H) | 222 222(GH)$^+$ |
| (35) | (in CD$_3$OD): δ 7.97(d, 2H), 7.49(d, 2H) | 222 222(GH)$^+$ |

\(G)$^+$ = guanidine$^+$ (i.e., $-\text{NHC}(=\text{NH})\text{NH}_2$); (GH)$^+$= protonated guanidine; (GH$_2$)$^+$ = double protonated guanidine; (G–H)$^+$ = loss of 1 proton from guanidine; (G + Na)$^+$ = guanidine plus sodium ion.

The compounds of the present invention may be prepared by known organic synthesis techniques, including the methods described in more detail in the Examples. In general, the compounds of this invention may be prepared by the following reaction scheme:

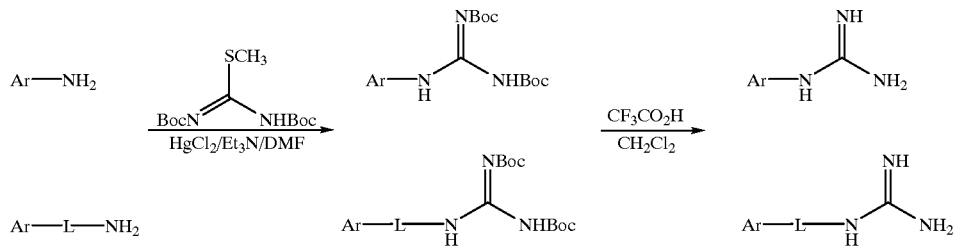

Pharmaceutically acceptable salts of the compounds of this invention may be made by techniques well known in the art, such as by reacting the free acid or base forms of these compounds with a stoichiometric amount of the appropriate base or acid in water of in an organic solvent. Suitable salts in this context may be found in *Remington's Pharmaceutical Sciences*, 17$^{th}$ ed., Mack Publishing Co., Easton, Pa., 1985, which is hereby incorporated by reference.

By way of example and not limitation, suitable pharmaceutically acceptable salts of the compounds of this invention include acid addition salts which may, for example, be formed by mixing a solution of the compound according to the invention with a solution of an acceptable acid such as hydrobromic acid, hydrochloric acid, fumaric acid, oxalic acid, p-toluenesulphonic acid, malic acid, maleic acid, methanesulfonic acid, succinic acid, acetic acid, citric acid, tartaric acid, carbonic acid, phosphoric acid, sulphuric acid and the like. The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. By way of example and not limitation, suitable pharmaceutically acceptable salts of the compounds of this invention include acid addition salts which may, for example, be formed by mixing a solution of the compound according to the invention with a solution of an acceptable acid such as hydrobromic acid, hydrochloric acid, fumaric acid, oxalic acid, p-toluenesulphonic acid, malic acid, maleic acid, methanesulfonic acid, succinic acid, acetic acid, citric acid, tartaric acid, carbonic acid, phosphoric acid, sulphuric acid and the like. The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

A compounds of this invention, or a pharmaceutically acceptable salt thereof, is administered to a patient in a therapeutically effective amount. A therapeutically effective amount is an amount calculated to achieve the desired effect. It will be apparent to one skilled in the art that the route of administration may vary with the particular treatment. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include intraarterial, intravenous, intradermal, intramuscular, subcutaneous, intraperitoneal, intrathecal and intraocular.

The required dosage may vary with the particular treatment and route of administration. In general, dosages for mitochondria protecting agents will be from about 1 to about 5 milligrams of the compound per kilogram of the body weight of the host animal per day; frequently it will be between about 100 μg and about 5 mg but may vary up to about 50 mg of compound per kg of body weight per day. Therapeutic administration is generally perfonred under the guidance of a physician, and pharmaceutical compositions contain the mitochondria protecting agent in a pharmaceutically acceptable carrier. These carriers are well known in the art and typically contain non-toxic salts and buffers. Such carriers may comprise buffers like physiologically-buffered saline, phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable nontoxic salts include acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate. maleate, acetate, citrate, benzoate. succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

In one embodiment of the invention, pharmaceutical compositions comprising one or more compounds of this invention are entrapped within liposomes. Liposomes are microscopic spheres having an aqueous core surrounded by one or more outer layer(s) made up of lipids arranged in a bilayer configuration (see, e.g., Chonn et al., *Current Op. Biotech.* 6:698, 1995). The therapeutic potential of liposomes as drug delivery aoents was recognized nearly thirty years ago (Sessa el al., *J. Lipid Res.* 9:310, 1968). Liposomes include "sterically stabilized liposome," a term which, as used herein, refers to a liposome comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen el al., *FEBS Letters* 223:42, 1987; Wu et al., *Cancer Research* 53:3765, 1993).

Various liposomes comprising one or more glycolipids are known in the art. Papahadjopoulos el al. (*Ann. N.Y Acad. Sci.*, 507:64, 1987) reported the ability of monosialoganglioside $G_{M1}$, galactocerebroside sulfate and phosphatidylinositol to improve blood half-lives of liposomes. These findings were expounded upon by Gabizon el al., *Proc. Natl Acad. Sci. U.S.A.* 85:6949, 1988). U.S. Pat. No. 4,837,028 and WO 88/04924, both to Allen et al., disclose liposomes comprising (1) sphingomyelin and (2) the ganglioside GM, or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Various liposomes comprising lipids derivatized with one or more hydrophilic polymers, and methods of preparation thereof, are known in the art. Sunamoto el al. (*Bull. Chem. Soc. Jpn.* 53:2778, 1980) described liposomes comprising a nonionic detergent, $2C_{12}15G$, that contains a PEG moiety. Illum et al. (*FEBS Letters* 167:79, 1984) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4.426,330 and 4,534, 899). Klibanov et al. (*FEBS Letts*. 268:235, 1990) described experiments demonstrating that liposomes comprising phosphatidylethanolamine (PE) derivatized with PEG or PEG stearate have significant increases in blood circulation half-lives. Blume el al. (*Biochimica et Biophysica Acta* 1029:91, 1990) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin el al. (U.S. Pat. No. 5,213,804 and European Pat. No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky el al.) Liposomes comprising PEG-modified ceramide lipids are described in WO 96/10391 (Choi el al.). U.S. Pat. Nos. 5,540,935 (Miyazaki et al.) and 5,556,948 (Tagawa et al.) describe PEG-containing liposomes that can be further derivatized with functional moieties on their surfaces.

When the compounds of the invention are prepared to treat chronic neurological disorders (such as, e.g., Alzheimer's disease) or acute necrotic events (such as, e.g., stroke), one preferred pharmaceutical composition is one in which a compound of the invention is encapsulated within a PEG-containing liposome that has been derivatized to include a factor that targets the liposome and its contents a portion of the central nervous system (CNS), such as, for example, the brain. Such a factor may be attached to the lipid bilayer of the liposome or to a PEG moiety that is incorporated into the liposome. By way of example and not limitation, one brain-targeting factor that can be used with PEG-containing liposomes is an antibody to a receptor that mediates uptake of one or more peptides through the blood brain barrier (BBB). Such peptides include, for example, insulin, insulin-like growth factors, transferrin and leptin. The antibody of the PEG-containing liposome, which may be a monoclonal antibody, targets the liposome and its contents to the brain via a specific interaction with a BBB peptide receptor such as e.g., the BBB transferrin receptor (Huwyler et al., *Proc. Natl. Acad.*

Sci. U.S.A. 93:14164–14169, 1996).

Mitochondria protecting agents of this invention also include prodrugs thereof. As used herein, a "prodrug" is any covalently bonded carrier that releases in vivo the active parent drug according the structure (I) when such prodrug is administered to the animal. Prodrugs of the compounds of structure (I) are prepared by modifying functional groups present on the compound in such a way that the modifications are cleaved, either in routine manipulation or in vivo, to the parent compound. Prodrugs include, but are not limited to, compounds of structure (I) wherein hydroxy, amine or sulfhydryl groups are bonded to any group that, when administered to the animal, cleaves to form the free hydroxyl, amino or sulfhydryl group, respectively. Representative examples of prodrugs include, but are not limited to, acetate, formate and benzoate derivatives of alcohol and amine functional groups.

The effectiveness of a compound as a mitochondria protecting agent may be determined by various assay methods. Suitable mitochondria protecting agents of this invention are active in one or more of the following assays for maintenance of mitochondrial structural and functional integrity, or in any other assay known in the art that measures the maintenance of mitochondrial structural and functional integrity. Accordingly, it is an aspect of the invention to provide methods for treating mitochondria associated diseases that include methods of administering compounds that may or may not have known antioxidant properties. However, according to this aspect of the invention, the unexpected finding is disclosed herein that mitochondria protecting agents may exhibit mitochondria protecting activities that are not predictable based upon determination of antioxidant properties in non-mitochondrial assay systems.

A. Assay for Inhibition of Production of Reactive Oxyoen Species Using Dichlorofluorescin Diacetate According to this assay, the ability of a mitochondria protecting agent of the invention to inhibit production of ROS intracellularly may be compared to its antioxidant activity in a cell-free environment. Production of ROS may be monitored using, for example by way of illustration and not limitation, 2',7'-dichlorodihydroflurescein diacetate ("dichlorofluorescin diacetate" or DCFC), a sensitive indicator of the presence of oxidizing species. Non-fluorescent DCFC is converted upon oxidation to a fluorophore that can be quantified fluorimetrically. Cell membranes are also permeable to DCFC, but the charged acetate groups of DCFC are removed by intracellular esterase activity, rendering the indicator less able to diffuse back out of the cell.

In the cell-based aspect of the DCFC assay for inhibition of production of ROS, cultured cells may be pre-loaded with a suitable amount of DCFC and then contacted with a mitochondria protecting agent. After an appropriate interval, free radical production in the cultured cells may be induced by contacting them with iron (III)/ascorbate and the relative mean DCFC fluorescence can be monitored as a function of time.

In the cell-free aspect of the DCFC assay for inhibition of production of ROS, a mitochondria protecting agent may be tested for its ability to directly inhibit iron/ascorbate induced oxidation of DCFC when the protecting agent, the fluorescent indicator and the free radical former are all present in solution in the absence of cells.

Comparison of the properties of a mitochondria protecting agent in the cell-based and the cell-free aspects of the DCFC assay may permit determination of whether inhibition of ROS production by a mitochondria protecting agent proceeds stoichiometrically or catalytically. Without wishing to be bound by theory. mitochondria protecting agents that scavenge free radicals stoichiometrically (e.g., on a one-to-one molecular basis) may not represent preferred agents because high intracellular concentrations of such agents might be required for them to be effective in vivo. On the other hand, mitochondria protecting agents that act catalytically may moderate production of oxygen radicals at their source, or may block ROS production without the agents themselves being altered, or may alter the reactivity of ROS by an unknown mechanism. Such mitochondria protecting agents may "recycle" so that they can inhibit ROS at substoichiometric concentrations. Determination of this type of catalytic inhibition of ROS production by a mitochondria protecting agent in cells may indicate interaction of the agent with one or more cellular components that synergize with the agent to reduce or prevent ROS generation. A mitochondria protecting agent having such catalytic inhibitory characteristics may be a preferred agent for use according to the method of the invention.

Mitochondria protecting agents that are useful according to the instant invention may inhibit ROS production as quantified by this fluorescence assay or by other assays based on similar principles. The person having ordinary skill in the art is familiar with variations and modifications that may be made to the assay as described here without departing from the essence of this method for determining the effectiveness of a mitochondria protecting agent, and such variations and modifications are within the scope of this disclosure.

B. Assay for Mitochondrial Permeability Transition (MPT) Using 2-,4-Dimethylaminostyryl-N-Methylpyridinium (DASPMI).

According to this assay, one may determine the ability of a mitochondria protecting agent of the invention to inhibit the loss of mitochondrial membrane potential that accompanies mitochondrial dysfunction. As noted above, maintenance of a mitochondrial membrane potential may be compromised as a consequence of mitochondrial dysfunction. This loss of membrane potential or mitochondrial permeability transition (MPT) can be quantitatively measured using the mitochondria-selective fluorescent probe 2-,4-dimethylaminostyryl-N-methylpyridinium (DASPMI).

Upon introduction into cell cultures, DASPMI accumulates in mitochondria in a manner that is dependent on, and proportional to, mitochondrial membrane potential. If mitochondrial function is disrupted in such a manner as to compromise membrane potential, the fluorescent indicator compound leaks out of the membrane bounded organelle with a concomitant loss of detectable fluorescence. Fluorimetric measurement of the rate of decay of mitochondria associated DASPMI fluorescence provides a quantitative measure of loss of membrane potential, or MPT. Because mitochondrial dysfumction may be the result of reactive free radicals such as ROS, mitochondria protecting agents that retard the rate of loss of DASPMI fluorescence may be effective agents for treating mitochondria associated diseases according to the methods of the instant invention.

C. Assays of Apoptosis in Cells Treated with Mitochondria Protecting Aents

As noted above, mitochondrial dysfunction may be an induction signal for cellular apoptosis. According to the assays in this section, one may determine the ability of a mitochondria protecting agent of the invention to inhibit or delay the onset of apoptosis. Mitochondrial dysfunction may be present in cells known or suspected of being derived from a subject with a mitochondria associated disease, or mitochondrial dysfunction may be induced in cultured normal or diseases cells by one or more of a variety of physical (e.g., UV radiation), physiological and biochemical stimuli with which those having skill in the art will be familiar.

Apoptosis and/or biochemical processes associated with apoptosis may also be using one or more "apoptogens," i.e., agents that induce apoptosis and/or associated processes when contacted with or withdrawn from cells or isolated mitochondria. Such apoptogens include by way of illustration and not limitation (1) apoptogens that are added to cells having specific receptors therefor, e.g., tumor necrosis factor (TNF). FasL, glutamate and NMDA; (2) withdrawal of growth factors from cells having specific receptors for such factors, such factors including, for example, IL-3 or corticosterone; and apoptogens that may be added to cells but which do not require a specific receptor, including (3) Herbimycin A (Mancini et al., *J. Cell. Biol.* 138:449–469, 1997), (4) Paraquat (Costantini et al., *Toxicology* 99:1–2, 1995); (5) ethylene glycols (http://www.ulaval.ca/vrr/rech/Proj/532866.html); (6) protein kinase inhibitors, such as, e.g.: Staurosporine, Calphostin C, d-erythro-sphingosine derivatives, Chelerythrine chloride. Genistein, 1-(5-isoquinolinesulfonyl)-2-methylpiperazine, KN-93, Quercitin, N-[2-((p-bromocinnamyl)amino)ethyl]-5-5-isoquinolinesulfonamide and caffeic acid phenethyl ester; (7) ionophores such as, e.g.: Ionomycin and valinomycin; (8) MAP kinase inducers such as, e.g.: Anisomycin and Anandamine; (9) cell cycle blockers such as, e.g.: Aphidicolin, Colcemid, 5-fluorouracil and homoharringtonine; (10) Acetylcholineesterase inhibitors such as, e.g.: berberine; (11) anti-estrogens such as, e.g.: Tamoxifen; (12) pro-oxidants, such as, e.g., tert-butyl peroxide and hydrogen peroxide; (13) free radicals such as, e.g., nitrous oxide; (14) inorganic metal ions, such as, e.g.: cadmium; (15) DNA synthesis inhibitors such as, for example, Actinomycin D, Bleomycin sulfate, Hydroxyurea, Methotrexate, Mitomycin C, Camptothecin. daunorubicin and intercalators such as, e.g., doxorubicin; (16) protein synthesis inhibitors such as, e.g., cyclohexamide, puromycin and rapamycin; (17) agents that affect microtubulin formation or stability such as, e.g., Vinblastine, Vincristine, colchicine, 4-hydroxyphenylretinamide and paclitaxel; (18) agents that raise intracellular calcium levels by causing the release thereof from intracellular stores, such as, e.g., thapsigargin (Thastrup et al., *Proc. Natl. Acad. Sci. U.S.A.* 87:2466–2470, 1990) and thpasigargicin (Santarius et al., *Toxicon* 25:389–399, 1987); and agents that are added to isolated mitochondria, such as (19) MPT inducers, e.g., Bax protein (Jurgenmeier et al., *Proc. Natl. Acad. Sci. U.S.A.* 95:4997–5002, 1998); and (20) calcium and inorganic phosphate (Kroemer et al., *Ann. Rev. Physiol.* 60:619, 1998).

In one aspect of the apoptosis assays, cells that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by those skilled in the art using light microscopy. As another example, cells undergoing apoptosis may exhibit fragmentation and disintegration of chromosomes, which may be apparent by microscopy and/or through the use of DNA specific or chromatin specific dyes that are known in the art, including fluorescent dyes. Such cells may also exhibit altered membrane permeability properties as may be readily detected through the use of vital dyes (e.g., propidium iodide, trypan blue) or the detection of lactate dehydrogenase leakage into the extracellular milieu. Damage to DNA may also be assayed using electrophoretic techniques (see, for example, Morris et al., *BioTechniques* 26:282–289, 1999). These and other means for detecting apoptotic cells by morphologic, permeability and related changes will be apparent to those familiar with the art.

In another aspect of the apoptosis assays, translocation of cell membrane phosphatidylserine (PS) from the inner to the outer leaflet of the plasma membrane is quantified by measuring outer leaflet binding by the PS-specific protein annexin (Martin et al, *J. Exp. Med.* 182:1545, 1995; Fadok et al., *J. Immunol.* 148:2207, 1992.). In a perferred format, exteriorization of plasma membrane PS is assessed in 96 well plates using a labeled annexin derivative such as an annexin-fluorescein isothiocyanate conjugate (annexin-FITC, Oncogene Research Products, Cambridge, Mass.).

In another aspect of the apoptosis assays. quantification of the mitochondrial protein cytochrome c that has leaked out of mitochondria in apoptotic cells may provide an apoptosis indicator that can be readily determined (Liu et al., *Cell* 86:147–157, 1996). Such quantification of cytochrome c may be performed spectrophotometrically, immunochemically or by other well established methods for detecting the presence of a specific protein. Release of cytochrome c from mitochondria in cells challenged with apoptotic stimuli (e.g., ionomycin, a well known calcium ionophore) can be followed by a variety of immunological methods. Matrix-assisted laser desorption ionization time of flight mass (MALDI-TOF) spectrometry coupled with affinity capture is particularly suitable for such analysis since apocytochrome c and holo cytochrome c can be distinguished on the basis of their unique molecular weights. For example, the SELDI system (Ciphergen, Palo Alto, USA) may be utilized to follow the inhibition by mitochondria protecting agents of cytochrome c release from mitochondria in ionomycin treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular weight of the protein is determined by its time of flight to the detector of the SELDI mass spectrometer.

In another aspect of the apoptosis assays, induction of specific protease activity in a family of apoptosis-activated proteases known as the caspases (Thornberry and Lazebnik, *Science* 281:1312–1316, 1998) is measured, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., 1997 *J Neurosci.* 17:6165). The labeled synthetic peptide Z-Tyr-Val-Ala-Asp-AFC, wherein "Z" indicates a benzoyl carbonyl moiety and AFC indicates 7-amino-4-trifluoromethylcoumarin (Kluck et al., 1997 *Science* 275:1132; Nicholson et al., 1995 *Nature* 376:37), is one such substrate. Another labeled synthetic peptide substrate for caspase-3 consists of two fluorescent proteins linked to each other via a peptide linker comprising the recognition/cleavage site for the protease (Xu et al., *Nucleic Acids Res.* 26:2034–2035, 1998). Other substrates include nuclear proteins such as UI-70 kDa and DNA-PKcs (Rosen and Casciola-Rosen, 1997 *J. Cell. Biochem.* 64:50; Cohen, 1997 *Biochem. J.* 326:1).

In another aspect of the apoptosis assays the ratio of living to dead cells, or the proportion of dead cells, in a population of cells exposed to an apoptogen is determined as a measure of the ultimate consequence of apoptosis. Living cells can be distinguished from dead cells using any of a number of techniques known to those skilled in the art. By way of non-limiting example, vital dyes such as propidium iodide or trypan blue may be used to determine the proportion of dead cells in a population of cells that have been treated with an apoptogen and a compound according to the invention (see Example 7).

The person of ordinary skill in the art will readily appreciate that there may be other suitable techniques for quantifying apoptosis, and such techniques for purposes of determining the effects of mitochondria protecting agents on the induction and kinetics of apoptosis are within the scope of the assays disclosed here.

D. Assay of Electron Transport Chain (ETC) Activity in Isolated Mitochondria.

As described above, mitochondria associated diseases may be characterized by impaired mitochondrial respiratory activity that may be the direct or indirect consequence of elevated levels of reactive free radicals such as ROS. Accordingly, a mitochondria protecting agent for use in the methods provided by the instant invention may restore or prevent further deterioration of ETC activity in mitochondria of individuals having mitochondria associated diseases. Assay methods for monitoring the enzymatic activities of mitochondrial ETC Complexes I, II, III, IV and ATP synthetase, and for monitoring oxygen consumption by mitochondria, are well known in the art. (See. e.g., Parker et al., Neurology 44:1090–96, 1994; Miller et al, J. Neurochem. 67:1897, 1996.) It is within the scope of the methods provided by the instant invention to identify a mitochondria protecting agent using such assays of mitochondrial function. Further, mitochondrial function may be monitored by measuring the oxidation state of mitochondrial cytochrome c at 540 nm. As described above, oxidative damage that may arise in mitochondria associated diseases may include damage to mitochondrial components such that cytochrome c oxidation state, by itself or in concert with other parameters of mitochondrial function including but not limited to mitochondrial oxygen consumption, may be an indicator of reactive free radical damage to mitochondrial components. Accordingly, the invention provides various assays designed to test the inhibition of such oxidative damage by mitochondria protecting agents. The various forms such assays may take will be appreciated by those familiar with the art and is not intended to be limited by the disclosures herein, including in the Examples.

For example by way of illustration and not limitation, Complex IV activity may be determined using commercially available cytochrome c that is fully reduced via exposure to excess ascorbate. Cytochrome c oxidation may then be monitored spectrophotometrically at 540 nm using a stirred cuvette in which the ambient oxygen above the buffer is replaced with argon. Oxygen reduction in the cuvette may be concurrently monitored using a micro oxygen electrode with which those skilled in the art will be familiar where such an electrode may be inserted into the cuvette in a manner that preserves the argon atmosphere of the sample, for example through a sealed rubber stopper. The reaction may be initiated by addition of a cell homogenate or, preferably a preparation of isolated mitochondria, via injection through the rubber stopper. This assay, or others based on similar principles, may permit correlation of mitochondrial respiratory activity with structural features of one or more mitochondrial components. In the assay described here, for example, a defect in complex IV activity may be correlated with an enzyme recognition site.

The following examples are offered by way of illustration, and not by way of limitation.

EXAMPLES

Example 1

Synthesis and Characterization of Represetative Agents

This example illustrates the synthesis and characterization of representative agents of this invention.

A. Synthesis of Aralkylaminoguanidines

1. Compound (1)

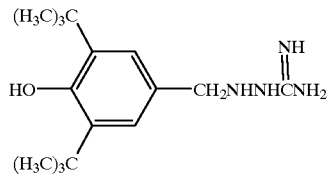

To 122 mg (0.5 mmole) of 3,5-di-tert-butyl-4-hydroxybenzaldehyde hemihydrate in 4 ml of acetic acid at room temperature was added aminoguanidine hydrochloride (110.6 mg, 1.0 mmol) and sodium cyanoborohydride (314 mg, 5 mmole) and the mixture was stirred overnight. The reaction mixture was then added to 50 ml of saturated sodium bicarbonate, and extracted with ethyl acetate (2×50 ml). The organic layer was dried over anhysrous sodium sulfate, and concentrated. The resulting solid was chromatographed over silica gel using chloroform/methanol/acetic acid (84:15:1) as eluting solvent to afford 94.8 mg of the product as the acetate salt in 54% yield. $^1$H NMR (500 MHz, CD$_3$OD): δ 7.14 (s, 2H), 3.83 (s, 2H), 1.97 (s, C$\underline{H}_3$COO$^-$), 1.42 (s, 18H)

2. Compound (4)

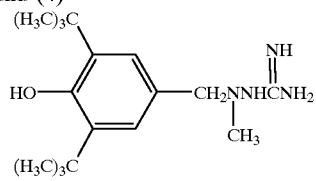

To 122 mg (0.5 mmole) of 3,5-di-tert-butyl-4-hydroxybenzaldehyde hemihydrate in 4 ml of acetic acid at room temperature was added aminoguanidine hydrochloride (110.6 mg, 1.0 mmol), 150 mg of paraformaldehyde and sodium cyanoborohydride (314 mg, 5 mmole) and the mixture was stirred overnight. The reaction mixture was then added to 50 ml of saturated sodium bicarbonate, and extracted with ethyl acetate (2×50 ml). The organic layer was dried over anhysrous sodium sulfate, and concentrated. The resulting solid was chromatographed over silica gel using chloroform/methanol/acetic acid (84:15:1) as eluting solvent to afford 119 mg of the product as the acetate salt in 65% yield. $^1$H NMR (500 MHz, CD$_3$OD): δ 7.12 (s, 2H), 3.87 (d, 1H), 3.59 (D, 1H), 2.68 (s, 3H), 1.96 (s, CH$_3$COO$^-$), 1.42 (s, 18H)

B. Representative Synthesis of Guanidine Compounds from Primary Amines

1. Compound (2)

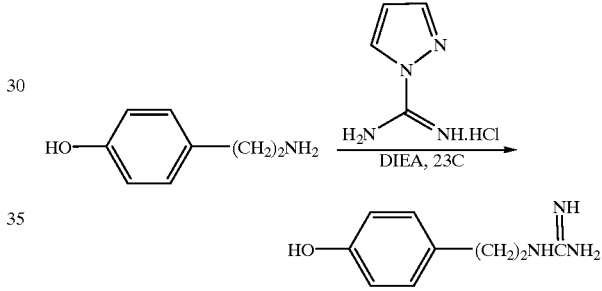

To tyramine (137 mg, 1 mmole) in 1 ml of DMF was added 1-H-pyrazole-1-carboximidine hydrochloride (146 mg, 1 mmole) and dilsopropylethylamine (DIEA) (174 μl, 1 mmole), and the reaction mixture was stirred at 23_for 16 hrs. The solvent was removed in vacuo under 40_C. The resulting crude material was chromatographed over silica gel using chloroform/methanol/acetic acid (84:15:1) as eluting solvent to furnish 159 mg ( 67%) of the desired product as the acetate salt. $^1$H NMR (500 MHz, CD$_3$OD): δ 7.07 (d, 2H, J=8.4 Hz), 6.74 (d, 2H, J=8.4 Hz), 3.39 (t, 2H, J=7 Hz), 2.78 (t, 2H, J=7 Hz), 1.97 (s, C$\underline{H}_3$COO$^-$).

2. Compound (5)

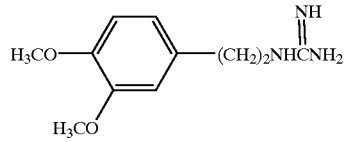

$^1$H NMR (500 MHz, CD$_3$OD): δ 6.89 (d, 1H, J=8.1 Hz), 6.87 (d, 1H, 1.9 Hz), (dd, 1H, J=8.1, 1.9 Hz), 3.83 (s, 3H, OC$\underline{H}_3$), 3.80 (s, 3H, OC$\underline{H}_3$), 3.43 (t, 2H, J=7.1 Hz 2.82 (t, 2H, J=7.1 Hz), 1.97 (s, CH$_3$COO$^-$).

C. Reaction Scheme for Preparing Arylguanidine Derivatives.

The following compounds were made according to the following reaction scheme:

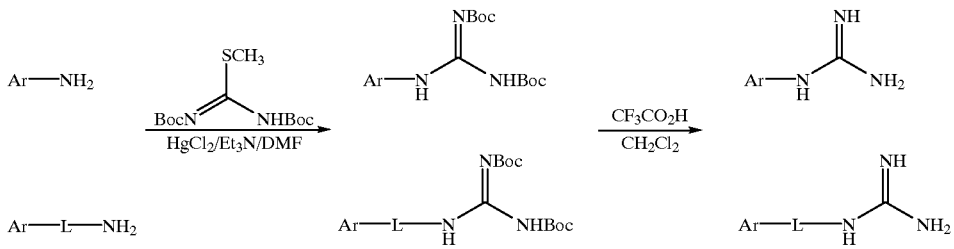

1. Compound (7)

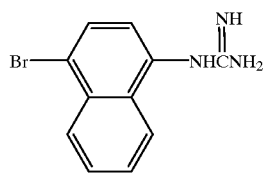

To a round-bottomed flask fitted with an argon inlet were placed 1-amino-4-bromonaphthalene (222 mg, 1.0 mmole), 1,3-bis(tert-butoxycarbonyl)-2-methyl-2-thiopseudourea (305 mg, 1.05 mmole) and dry N,N-dimethylformamide (5 ml). To the above stirred solution at room temperature were added triethylamine (0.42 ml, 3.0 mmole) and mercuric chloride (298 mg, 1.1 mmole). The resulting mixture was stirred at room temperature, whereupon a white precipitate soon formed. After stirring for 3 h, the reaction mixture was diluted with ethyl acetate and filtered through a pad of Celite. The filtrate was washed with 5% aqueous sodium carbonate (1×20 ml), water (2×20 ml) and brine (1×20 ml). The solution was dried over anhydrous magnesium sulfate and concentrated to provide the crude product. Purification by flash chromatography using 12% ethyl acetate/hexane provided 289 mg of the Boc-protected guanidine derivative in 62% yield. $^1$H NMR (500 MHz, CD$_3$OD): δ 8.27 (m, 1H), 8.02 (m, 2H), 7.84 (d, 1H, J=8.1 Hz), 7.71 84 (d, 1H, J=8.1 Hz), 7.67 (m, 2H), 1.61 (s, 9H), 1.35 (s, 9H).

Deprotection of the Boc group was achieved by treatment with trifluoroacetic acid (TFA). Thus, to 51 mg (0.11 mmole) of the naphthyl derivative under argon was added 1 ml of 50% TFA/CH$_2$CL$_2$ solution and the mixture was stirred for 3 h at 23° C. The solvent was then removed by rotary evaporation. The crude product was purified by flash chromatography using chloroform/methanol/acetic acid (81:18:1) as eluting solvent to provided 30 mg of the acetate salt of 4-bromo-1-guanidino-naphthalene in 85% yield. $^1$H NMR (500 MHz, CD$_3$OD): δ 7.93 (dd, 1H, J=6.6, 2.1 Hz), 8.01 (dd, 1H, J=6.6, 2.1 Hz), 7.92 (d, 1H, J=8 Hz), 7.74 (m, 2H), 7.42 (d, 1H, J =7.7 Hz), 1.95 (s, C$\underline{H}_3$COO$^-$).

2. Compound (10)

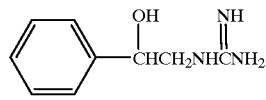

$^1$H NMR (500 MHz, CD$_3$OD): δ 7.42 (m, 2H), 7.37, (m, 2H), 7.30 (m, 1H), 4.83 (m, 1H), 3.43 (dd, 1H, J=3.7, 13.9 Hz), 3.35 (dd, 1H, J=7.5, 13.9 Hz).

3. Compound (6)

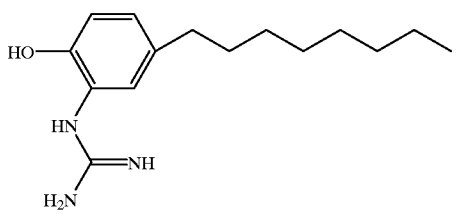

$^1$H NMR (500 MHz, CD$_3$OD): δ 7.04 (dd, 1H, J=2.1, 8.3 Hz), 6.98 (d, 1H, J=2.1 Hz), 6.87 (d, 1H, J=8.3 Hz), 2.54 (t, 2H, 7.6 Hz), 1.58 (br. t, 2H), 1.30 (m, 10 H), 0.89 (t, 3H, J=7 Hz).

Example 2

DCFC Assay for Inhibition of ROS Production by Mitochondria Protecting Agent In the cell-based aspect of the DCFC assay, monolayers of cultured adherent SH-SY5Y human neuroblastoma cells (Biedler et al., Cancer Res. 33:2643, 1973) at or near confluence are rinsed and harvested using trypsin according to standard methods. Single cell suspensions containing 7.5×10$^4$ cells in 200 μl of medium are seeded into 96-well plates for overnight incubation at 37° C. and 5% CO$_2$ in a humidified cell atmosphere. The following day the wells are gently rinsed once with warm Hanks balanced saline solution (HBSS, Gibco-BRL), 200 μl of 30 μM dichlorofluorescin-diacetate (DCFC-DA, Molecular Probes, Eugene, Oreg.) are added to each well and cultures are incubated for 2 hours at 37° C./5% CO$_2$. The excess DCFC-DA is removed by needle aspiration and each well is gently rinsed twice with HBSS. Each well then receives 80 μl of HBSS and 10 μl of mitochondria protecting agent, or vehicle control diluted into HBSS from stock solutions of dimethylformamide or dimethylsulfoxide. The final concentration of the organic solvent is maintained at or below 0.1% (v/v) in HBSS while in contact with cells.

Cells are equilibrated for 15 minutes at room temperature with the mitochondria protecting agent (or vehicle control) and then 10 μl of fresh 500 μM ferric chloride/300 μM ascorbate solution is added to initiate free radical formation. Fluorescence of each microculture in the 96-well plate is quantified immediately using a Cytofluor fluorimetric plate reader (model #2350, Millipore Corp., Bedford, Mass.; excitation wavelength=485 nm; emission wavelength=530 nm) and to fluorescence is recorded. The 96-well plates are incubated 30 minutes at 37° C./5% CO$_2$ and fluorescence at 530 nm is again measured (t$_{30}$). The change in relative mean fluorescence (RMF) over the 30 minute period is calculated for each well.

The cells are then harvested by trypsinization and counted using a hemacytometer in order to normalize the data as $\Delta(t_{30}-t_0)$RMF per cell. The efficacy of a candidate mitochondria protecting agent is determined by comparing its ability to inhibit ROS production relative to the vehicle control.

In the cell-free aspect of the DCFC assay, candidate mitochondria protecting agents are further evaluated for their ability to inhibit ROS oxidation of DCFC in solution in a microtitre plate format. Stock compound solutions are usually prepared in dimethylformamide (DMF) or dimethylsulfoxide (DMSO) and diluted further into working concentrations using HBSS. Inhibition studies are carried out over a range of concentrations. Ten $\mu$l of the compound solution or vehicle control and 10 $\mu$l of a 300 $\mu$M DCFC solution in HBSS buffer are added to 60 $\mu$l of YIBSS buffer. Ten $\mu$l of fresh 500 $\mu$M ferric chloride/300 $\mu$M ascorbate solution is then added to initiate free radical formation. Fluorescence of each well in the 96-well plate is quantified immediately using a Cytofluor fluorimetric plate reader (model #2350, Millipore Corp., Bedford, Mass.; excitation wavelength=485 nm; emission wavelength=530 nm) and to fluorescence is recorded. Ten $\mu$l of a 0.5% aqueous $H_2O_2$ solution is then added to initiate hydroxyl radical formation through Fenton chemistry and a second fltuorimetric reading is taken after 10 min. The concentration at which a candidate mitochondria protecting agent exerts 50% of its maximal inhibitory activity ($IC_{50}$) is calculated from a two-dimensional plot of relative fluorescence units against inhibitor concentration.

Example 3

Assay for Mitochondrial Permeability Transition Using DASPMI

The fluorescent mitochondria-selective dye 2-,4-dimethylaminostyryl-N-methylpyridinium (DASPMI, Molecular Probes, Inc., Eugene, Oreg.) is dissolved in HBSS at 1 mM and diluted to 25 $\mu$M in warm HBSS. In 96-well microculture plates, cultured human cytoplasmic hybrid ("cybrid") cells produced by fusing mitochondrial DNA depleted ($\rho^0$) SY5Y cells and mitochondria source platelets (Miller et al., J. Neurochem. 67:1897–1907, 1996) from an individual known or suspected of having a mitochondria associated disease, or from normal (control) platelets, are incubated for 0.5–1.5 hrs in 25 $\mu$M DASPMI in a humidified 37° C./5% $CO_2$ incubator to permit mitochondrial uptake of the fluorescent dye. Culture supernatants are then removed and various concentrations of candidate mitochondria protecting agents diluted into HBSS from DMF stocks, or vehicle controls, are added at various concentrations. Mitochondria protecting agents are introduced to cells either before, or at the same time as, introduction of the cells to ionomycin (described below).

Fluorescence of each microculture in the 96-well plate is quantified immediately using a Molecular Devices ƒmax™ fluorimetric plate reader (Molecular Devices Corp., Sunnyvale, Calif.; excitation wavelength=485 nm; emission wavelength=590 nm) and to fluorescence is recorded. Thereafter, induction of mitochondrial membrane potential collapse is initiated by the addition of ionomycin (Calbiochem, San Diego, Calif). Ionomycin stock solutions of various concentrations from 0.1–40 $\mu$M are prepared in warm Hank's balanced salt solution (HBSS) and diluted for addition to cells to achieve a final concentration of 0.05–20 $\mu$M, with final concentrations of 4–10 $\mu$M being preferred. Fluorescence decay of DASPMI-loaded, ionomycin induced cells is monitored as a function of time from 0–500 seconds following addition of ionomycin. The maximum negative slope (V–max) is calculated from a subset of the data using analysis software provided by the fluorimetric plate reader manufacturer. In addition, the initial and final signal intensities are determined and the effects of candidate mitochondria protecting agents on the rate of signal decay are quantified.

Representative data providing $IC_{50}$ values of mitochondria protecting agents are presented below in Table 3.

TABLE 3

| $IC_{50}$ Values for Representative Compounds | |
|---|---|
| Compound | $IC_{50}$ Cell ($\mu$M) |
| Creatine | 2000 |
| Cyclocreatine | 3000 |
| 4-Guanidinobenzoic Acid | 1000 |
| (2) | 100 |
| (4) | 10 |
| (11) | 100 |

Example 4

Effect of Agent of Apoptosis

In 96-well microculture plates, cultured human cells from an individual known or suspected of having a mitochondria associated disease, or normal (control) cells or cell lines, are cultured for a suitable period in the presence or absence of physiological inducers of apoptosis (e.g., Fas ligand, TNF-$\alpha$, or other inducers of apoptosis known in the art) and in the presence or absence of representative compounds of this invention.

Exteriorization of plasma membrane phosphatidyl serine (PS) is assessed by adding to the 96 well plate annexin-fluorescein isothiocyanate conjugate (annexin-FITC, Oncogene Research Products. Cambridge, Mass.) dissolved in a suitable buffer for binding to cell surfaces at a final concentration of 5 $\mu$g/well. (Martin et al., J. Exp. Med. 182:1545, 1995) After 15–30 min in a humidified 37° C./5% $CO_2$ incubator, cells are fixed in situ using 2% formalin, washed to remove non-specifically bound FITC and read using a Cytofluor fluorimetric plate reader (model #2350, Millipore Corp., Bedford, Mass.; excitation wavelength=485 nm; emission wavelength=530 nm) to quantify cell surface bound annexin-FITC as a measure of outer leaflet PS, a marker for cells undergoing apoptosis.

Caspase-3 activity is assessed by diluting the fluorogenic peptide substrate Asp-Glu-Val-Asp-AMC (DEVD-AMC) from a DMSO stock solution into culture media to a final concentration of 20 $\mu$M for uptake by cells. Substrate cleavage liberates the fluorophore, which is measured continuously using a Cytofluor fluorimetric plate reader (model #2350, Millipore Corp., Bedford, Mass.; excitation wavelength=4355 nm; emission wavelength=460 nm). Caspase-1 is measured using the same protocol as that for caspase-3, except the caspase-1 specific fluorogenic substrate Tyr-Val-Ala-Asp-Z (Z-YVAD), is substituted for DEVD-AMC and fluorimetry is conducted using 405 nm excitation and 510 nm emission.

Cytochrome c released from mitochondria of cells undergoing apoptosis is recovered from the post-mitochondrial supernatant and quantified by reverse phase HPLC using a C-18 column, gradient elution (0–45% methanol in phosphate buffer, pH 7.4) and UV absorbance at 254 nm.

Commercially-obtained authentic cytochrome c serves as the standard. Recovered cytochrome c is also quantified immunochemically by immunoblot analysis of electrophoretically separated post-mitochondrial supernatant proteins from apoptotic cells, using cytoclirome c-specific antibodies according to standard and well accepted methodologies.

Example 5

Effect of Representative Compound on Ionomycin-Induced Apoptosis in Neuroblastoma Cells SH-SY5Y neuroblastoma cells ($1 \times 10^5$ cells) were rinsed with one volume 1X PBS, and then treated with 10 $\mu$M ionomycin (Calbiochem, San Diego, Calif.) in DMEM supplemented with 10% fetal calf serum (FCS) (Gibco, Life Technologies, Grand Island, N.Y.) for 10 minutes, followed by two washes with DMEM (10% FCS). After 6 h incubation at 37° C. in DMEM (10% FCS), cells were visualized by light microscopy (20×magnification). Approximately 80% of ionomycin treated cells exhibited membrane blebbing, indicative of entry by those cells into a final stage of apoptosis, compared to negligible apoptosis (<5%) in untreated cells. When cells were simultaneously treated with ionomycin and 2 mM creatine, the proportion of cells undergoing apoptosis as evidenced by membrane blebbing was reduced to approximately 10%. Compound (11) at 100 $\mu$M provides the same magnitude of protection from induction of apoptosis as did 2 mM creatine in this ionomycin induced apoptosis assay.

Example 6

Effect of Representative Compound on Ionomycin Induces Apoptosis in Cybrid Cells Control cybrid cells (MixCon) produced by fusing $\rho^0$ SH-SY5Y neuroblastoma cells with mitochondria source platelets from normal subjects, and 1685 cells, a cybrid cell line produced by fusing $\rho^0$ SH-SY5Y cells with mitochondria source platelets from an Alzheimer's Disease patient (Miller et al., *J. Neurochem.* 67:1897–1907, 1996), were grown to complete confluency in 6-well plates (~$3 \times 10^6$ cells/well). Cells were first rinsed with one volume 1×PBS, and then treated with 10 $\mu$M ionomycin in the absence or presence of 100 $\mu$M compound (12), in DMEM supplemented with 10% FCS, for 1 minute. At one minute, cells were rinsed twice with five volumes of cold 1×PBS containing a cocktail of protease inhibitors (2 $\mu$g/ml pepstatin, leupeptin, aprotinin, and 0.1 mM PMSF). Cells were then collected in one ml of cold cytosolic extraction buffer (210 mM mannitol, 70 mM mannitol, 5 mM each of HEPES, EGTA, glutamate and malate, 1 mM $MgCl_2$, and the protease inhibitor cocktail at the concentrations given above. Homogenization was carried out using a type B dounce homogenizer, 25× on ice. Cells were spun at high speed in an Eppendorf microfuge for five minutes to separate cytosol from intact cells, as well as cell membranes and organelles. The supernatant was collected and an aliquot was saved, along with the pellet, at −80° C. for citrate synthase and protein assays.

Cytochrome c antibody was covalently bound to solid support chips containing a pre-activated surface (ProteinChip, Ciphergen, Palo Alto, Calif.). The spot to be treated with antibody was initially hydrated with 1 $\mu$l of 50% $CH_3CN$ and the antibody solution was added before the $CH_3CN$ evaporated. The concentration of the antibody was approximately 1 mg/ml in either $Na_3PO_4$ or PBS buffer (pH 8.0). The chip was placed in a humid chamber and stored at 4° C. overnight. Prior to addition of the cytosolic extract, residual active sites were blocked by treatment with 1.5 M ethanolamine (pH 8.0) for thirty minutes. The ethanolamine solution was removed and the entire chip was washed in a 15 ml conical tube with 10 ml 0.05% Triton-X 100 in 1×PBS, for 5 minutes with gentle shaking at room temperature. The wash buffer was removed and the chip was sequentially washed, first with 10 ml 0.5 M NaCl in 0.1 M NaOAc (pH 4.5), and then with 0.5 M NaCl in 0.1M Tris (pH 8.0). After removal of the Tris-saline buffer, the chip was rinsed with 1×PBS and was ready for capture of the antigen.

Fresh supernatant samples were spotted onto the Ciphergen ProteinChip containing covalently-linked anti-cytochrome c antibody (Pharmingen, San Diego, Calif.). For optimal antibody-cytochrome c interaction, 100 $\mu$l of the supernatant was used and the incubation was carried out overnight with shaking at 4° C. in a Ciphergen bioprocessing unit. The supernatant was then removed and the spots on the chip were washed in the bioprocessing unit three times with 200 $\mu$l of 0.1% Triton-X 100 in 1×PBS, and then twice with 200 $\mu$l of 3.0 M urea in 1×PBS. The chips were then removed from the bioprocessor and washed with approximately 10 ml of $dH_2O$. The chips were then dried at room temperature prior to the addition of EAM solution (e.g., sinapinic acid, Ciphergen, Palo Alto, Calif.). A suspension of the EAM was made at a concentration of 25 mg/ml in 50% $CH_2CN/H_2O$ containing 0.5% TFA. The saturated EAM solution was clarified by centrifugation and the supernatant was used for spotting on the ProteinChip surface. Prior to the addition of EAM to the chip, an internal standard of ubiqutin was added to the EAM solution to provide a final concentration of 1 pmol/$\mu$l. The quantification of cytochrome c released from mitochondria upon ionomycin treatment was based on normalization to the ubiquitin peak in the mass spectrum and the protein content of the cytosolic extracts. Citrate synthase activity of cytosolic extracts was measured to rule out the possibility of mitochondrial lysis during the sample preparation procedure.

Representative data depicting cytoclrome c release in cells undergoing ionomycin induced apoptosis, and attenuation of cytochrome release in cells treated with 100 $\mu$M compound (11) at the same time ionomycin was introduced, are presented in the FIGURE.

Example 7

Effect of representative Compounds on Thapsigargin Induced Apoptosis

In order to determine the effect of compounds of this invention on the final endpoint of apoptosis (cell death), the following assays were carried out. The cells used were 1685 cells, "1685" being the designation of a cybrid cell line derived from SH-SY5Y and containing mitochondria from a patient having Alzheimer's disease (see U.S. Pat. No. 5,888, 498, issued Mar. 30, 1999, hereby incorporated by reference). Cells were plated ($3 \times 10^4$ cells per well) on 96-well plates 48 hours prior to thapsigargin treatment. Thapsigargin (Calbiochem, La Jolla, Calif.) alone (final concentration, 1 $\mu$M), thapsigargin (1 $\mu$M) plus agent final concentration, 100 $\mu$M), agent alone (100 $\mu$M) in growth media, or growth media devoid of both thapsigargin and agent, were added to cells in four separate wells.

Twenty-four hours after thapsigargin +/− agent treatment, propidium iodide (Sigma Chemical Co., St. Louis, Mo.) was added to each well at a final concentration of 10 µg/ml per well. The cells were incubated at ambient temperature for 10 minutes, after which the fluorescence (excitation max=536 nm, 544 nm used for excitation; emission max=617, readings at 612 nm) was determined for each individual well in a ƒmax™ fluorescence microplate reader (Molecular Devices, Sunnyvale, Calif.). The resulting fluorescence values correspond to cells in the monolayer of a well that are non-viable.

Next, the media was aspirated, and the monolayer was fixed (killed) by adding 100 µl of 100% ethanol to each well followed by incubation at ambient temperature for minutes. The fluorescense in each well was then read again. The fluorescence values resulting from the second reading correspond to the total number of cells (whether viable or non-viable at the time of the initial fluorescence reading) present in the monolayer of a well.

The results, presented in Table 4 below, are expressed as the percentage of non-viable cells as a proportion of the viable cells (fixed controls).

TABLE 4

Effect of Representative Compounds on Thapsigargin-Induced Apoptosis

| Cpd. No. | % Non-Viable Cells with Thapsigargin and without Cmpd. | % Non-Viable Cells with Thapsigargin and with Cmpd. | Δ Cell Viability[1] | P-Value[2] |
|---|---|---|---|---|
| (1) | 41.5 | 38.3 | 3.2 | 0.0978 |
| (3) | 41.7 | 46.7 | −5.0 | 0.2120 |
| (4) | 45.9 | 43.8 | 2.1 | 0.5908 |
| (6) | 44.0 | 122.1 | −78.1 | <0.0001 |
| (9) | 49.6 | 42.0 | 7.6 | 0.1794 |
| (11) | 36.0 | 29.0 | 7.0 | 0.0977 |
| (12) | 39.3 | 37.5 | 1.8 | 0.3268 |
| (13) | 37.0 | 52.8 | −15.8 | <0.0001 |
| (14) | 44.4 | 47.9 | −3.5 | 0.0681 |
| (15) | 39.1 | 42.2 | −3.1 | 0.1132 |
| (16) | 46.6 | 121.2 | 74.6 | <0.0001 |
| (17) | 45.2 | 56.9 | −11.7 | <0.0001 |
| (18) | 46.5 | 47.8 | −1.3 | 0.5853 |
| (19) | 41.9 | 44.3 | −2.4 | 0.3963 |
| (20) | 45.4 | 48.9 | −3.5 | 0.2714 |
| (21) | 44.1 | 43.8 | 0.3 | 0.9418 |
| (22) | 47.8 | 53.8 | −6.0 | 0.0015 |
| (23) | 50.4 | 49.8 | 0.6 | 0.7626 |
| (24) | 47.8 | 47.1 | 0.7 | 0.7476 |
| (25) | 52.0 | 48.9 | 3.1 | 0.3249 |
| (26) | 50.7 | 38.0 | 12.7 | <0.0001 |
| (27) | 50.4 | 42.5 | 7.9 | 0.0273 |
| (28) | 48.8 | 52.3 | −3.5 | 0.0950 |
| (29) | 45.7 | 48.6 | −2.9 | 0.0908 |
| (30) | 47.3 | 36.5 | 10.8 | <0.0001 |
| (31) | 45.3 | 100.0 | −54.7 | <0.0001 |
| (32) | 45.8 | 45.7 | 0.1 | 0.9352 |
| (33) | 50.6 | 49.2 | 1.4 | 0.6732 |
| (34) | 45.3 | 42.4 | 2.9 | 0.1743 |
| (35) | 45.1 | 42.3 | 2.8 | 0.0865 |

[1][% Non-Viable Cells (with Thapsigargin, without Cmpd)] − [% Non-Viable Cells (with Thapsigargin, with Cmpd)].
[2]Fischer's PLSD; significant result if < 0.05.

The data presented in Table 4, and other results from these experiments, define classes of compounds, i.e., (1) anti-apoptotic or thapsigargin protective agents; (2) pro-apoptotic or thapsigargin enhancing agents: (3) cytotoxic agents; and (4) agents that have little or no impact on the apoptotic effects of thapsigargin. Each of these classes of compounds is described in more detail infra.

Class 1: Anti-apoptotic or Thapsigarin Protective Agents.

These agents have a ΔCell Viability that is a positive number; this indicates that a lower percentage of cells undergo apoptosis due to thapsigargin treatment when the agent is present than when it is not. Agents in Class 1 include Compounds (11), (9), (30), (27), and (26). These compounds have a ΔCell Viability value≧about +4.5.

Class 2: Pro-apoptotic or Thapsigargin enhancing Agents.

These agents have a ΔCell Viability that is a negative number, which indicates that a higher percentage of cells undergo apoptosis due to thapsigargin treatment when the agent is present than when it is not. Agents in Class 2 include Compounds (22) and (3). These compounds have a ΔCell Viability value ≦−4.5 and ≧ about −10.

Class 3: Cytotoxic Agents.

These agents have a ΔCell Viability in the presence of thapsigargin that is a large negative number, which might indicate that these agents are strongly proapoptotic or thapsigargin enhancing agents, i.e., that a much higher percentage of cells undergo apoptosis due to thapsigargin treatment when the agent is present than when it is not. However, because these agents significantly increase the percentage of non-viable cells even in the absence of thapsigargin (see Table 4 below), they are designated cytotoxic agents. Agents in Class 3 include Compounds (6), (31), (17), (16) and (13). These compounds have a ΔCell Viability [(+thapsigargin, −compound)—(+thapsigargin, +compound)] value≦about −10, ranging from about −12 to −16 (Compounds (17) and (13)) down to about −55 (Compound (31)) and about −75 to −80 (Compounds (6) and (16)) and lower.

The cytotoxic nature of these compounds is revealed by the ΔCell Viability values resulting from treatment of cells with the compound in the absence of thapsigargin, as detailed in Table 5. The ΔCell Viability values resulting from treating cells with agents in this class in the absence of thapsigaroin (Table 4, infra) closely parallel the ΔCell Viability values that result when cells are treated with the respective agent and thapsigargin (Table 4, supra). This indicates that compounds in this class exert their effect predominately by being cytotoxic, and that they may have little or no thapsigargin enhancing activity. In contrast, agents in Classes 1, 2 and 4 do not exhibit these cytotoxic effects.

TABLE 5

Cytotoxic Effects of Representative Compounds (No Thapsigargin)

| Cpd. No. | % Non-Viable Cells without Cmpd. | % Non-Viable Cells with Cmpd. | Δ Cell Viability[1] | P-Value[2] |
|---|---|---|---|---|
| (6) | 16.2 | 125.2 | −109.0 | <0.0001 |
| (13) | 17.2 | 39.4 | −22.2 | <0.0001 |
| (16) | 17.0 | 123.7 | −106.7 | <0.0001 |
| (17) | 17.7 | 41.3 | −23.6 | <0.0001 |
| (31) | 16.5 | 100.0 | −83.5 | <0.0001 |

[1][% Non-Viable Cells (without Cmpd)] − [% Non-Viable Cells (with Cmpd)].
[2]Fischer's PLSD; significant result if < 0.05.

Class 4: Agents Having Little or no Effect on Thapsiargin Induced Apoptosis.

These agents have ΔCell Viability values that relatively small positive or negative numbers, which indicates that the percentage of cells undergoing apoptosis due to thapsigargin treatment when the agent is present is not much different than when it is not. Compounds in Class 4 have a ΔCell Viability value ranging from about 3.5 (Compound (1)) to about −3.5 (Compounds (20) and (14)).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating a mitochondria-associated disease by administering to a warm-blooded animal in need thereof an effective amount of a compound having the following structure:

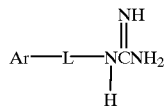

including stereoisomers, prodrugs and pharmaceutically acceptable salts thereof,
wherein:
Ar is phenyl or naphthyl optionally substituted with 1 to 5 $R_2$ groups;
L is an optional linker moiety selected from —$(CH_2)_n$—, —$(CH_2)_n NH$—, —$(CH_2)_n N(C_{1-4}alkyl)$—, —$NHC(=NH)$— and —$(CH_2)_n O(CH_2)_n$—, wherein n is 1–4 and each linker moiety is optionally substituted with 1 to 5 $R_3$ groups;
$R_2$ is hydroxy, $C_{1-2}$alkyl, $C_{1-2}$alkyloxy, halo, —$NH2$, —NHR, —NRR, cyano, nitro, —SR, —COOH, $C_{7-12}$,aralkyl or heterocycle; or $C_{1-12}$alkyl, $C_{1-12}$alkyloxy, —$NH_2$, —NHR, —NRR, —SR, $C_{7-12}$aralkyl or heterocycle substituted with 1 to 5 $R_3$ groups;
$R_3$ is hydroxy, halo, $C_{1-4}$alkyl, —OR, —$NH_2$, —NHR or —NRR; and
each occurrence of R is independently selected from $C_{1-4}$alkyl.

2. The method of claim 1 wherein Ar is phenyl optionally substituted with 1 to 5 $R_2$ groups.

3. The method of claim 2 wherein Ar is phenyl, 3,5-di-t-butyl-4-hydroxyphenyl, 2-methoxy-4-carboxylphenyl, 2-chloro-4-carboxyl-5-methoxyphenyl, 3,5-di-tetrafluoromethylphenyl, 3 5-difluorophenyl, 3,4,5-trimethoxyphenyl, 4-n-hexoxyphenyl, 4-fluorophenyl, 3-trifluorophenyl, 2-carbinolphenyl, 2-chloro-5-methylphenyl, 3-carboxylphenyl, 3-carboxyl-4-hydroxyphenyl, 2-methyl-4-carboxylphenyl, 4-methoxyphenyl, 2-hydroxyphenyl, 4-(N-morphinol) phenyl, 3,4-dihydroxyphenyl, 2,4-dimethylphenyl, 2-methyl-4-hydroxyphenyl, 4-n-octylphenyl, 2-hydroxy-5-n-octylphenyl, 4-chlorophenyl, or 2-methyl-4-chlorophenyl.

4. The method of claim 1 wherein Ar is naphthyl optionally substituted with 1 to 5 $R_2$ groups.

5. The method of claim 4 wherein Ar is naphthyl or 4-bromonaphthyl.

6. The method of claim 1 wherein the L is not present.

7. The method of claim 1 wherein L is present.

8. The method of claim 7 wherein L is —$CH_2NH$—, —$CH_2CH_2$—, —$CH(OH)CH_2$—, —$CH_2N(CH_3)$— or —$NHC(=NH)$—.

9. The method of claim 1 wherein the compound is administered in the form of a pharmaceutical composition.

10. The method of claim 1 wherein the mitochondria-associated disease is a disease in which free radical mediated oxidative injury leads to tissue degeneration.

11. The method of claim 1 wherein the mitochondria-associated disease is a disease in which cells inappropriately undergo apoptosis.

12. The method of claim 1 wherein the mitochondria-associated disease is a disease in which cells fail to undergo apoptosis.

13. The method of claim 12 wherein the mitochondria-associated disease is cancer.

14. The method of claim 1 wherein the mitochondria-associated disease is stroke.

15. The method of claim 1 wherein the mitochondria-associated disease is Alzheimer's Disease.

16. The method of claim 1 wherein the mitochondria-associated disease is diabetes.

17. The method of claim 1 wherein the mitochondria-associated disease is auto-immune disease.

18. The method of claim 1 wherein the mitochondria-associated disease is psoriasis.

19. The method of claim 1 wherein the mitochondria-associated disease is Alzheimer's Disease.

20. The method of claim 1 wherein the mitochondria-associated disease is Parkinson's Disease.

21. The method of claim 1 wherein the mitochondria-associated disease is Huntington's Disease.

22. The method of claim 1 wherein the mitochondria-associated disease is auto-immune disease.

23. The method of claim 1 wherein the mitochondria-associated disease is Type I or Type II diabetes mellitus.

24. The method of claim 1 wherein the mitochondria-associated disease is congenital muscular dystrophy.

25. The method of claim 1 wherein the mitochondria-associated disease is fatal infantile myopathy or later-onset myopathy.

26. The method of claim 1 wherein the mitochondria-associated disease is MELAS (Mitochondrial Encephalopathy, Lactic Acidosis, and Stroke).

27. The method of claim 1 wherein the mitochondria-associated disease is MIDD (Mitochondrial Diabetes and Deafness).

28. The method of claim 1 wherein the mitochondria-associated disease is MERFF (Moclonic Epilepsy ragged Red Fiber Syndrome).

29. The method of claim 1 wherein the mitochondria-associated disease is arthritis.

30. The method of claim 1 wherein the mitochondria-associated disease is NARP (Neuropathy, Ataxia, Retinitis Pigmentosa).

31. The method of claim 1 wherein the mitochondria-associated disease is MNGIE (Myopathy and external ophthalmoplegia, Neuropathy, Gastro-Intestinal, Encephalopathy).

32. The method of claim 1 wherein the mitochondria-associated disease is LHON (Leber's, Hereditary, Optic, Neuropathy).

33. The method of claim 1 wherein the mitochondria-associated disease is Kearns-Sayre disease.

34. The method of claim 1 wherein the mitochondria-associated disease is Pearson's Syndrome.

35. The method of claim 1 wherein the mitochondria-associated disease is PEO (Progressive External Ophthalmoplegia).

36. The method of claim 1 wherein the mitochondria-associated disease is Wolfram syndrome.

37. The method of claim 1 wherein the mitochondria-associated disease is DIDMOAD (Diabetes Insipidus, Diabetes Mellitus, Optic Atrophy, Deafness).

38. The method of claim 1 wherein the mitochondria-associated disease is Leigh's Syndrome.

39. The method of claim 1 wherein the mitochondria-associated disease is dystonia.

40. The method of claim 1 wherein the mitochondria-associated disease is schizophrenia.

* * * * *

UNITED STATES PATENT AND TRADEMARK OFFICE
CERTIFICATE OF CORRECTION

PATENT NO. : 6,268,398 B1
DATED : July 31, 2001
INVENTOR(S) : Soumitra Ghosh and Robert E. Davis It is certified that error appears in the above-identified patent and that said Letters Patent is hereby corrected as shown below:

Title page,
Item [56], References Cited, "Anderson,"Mitochondrial Dysfunction in Diabetes Mellitus," *Drug Development Research* 46:67-79m 19999." should be corrected to read as -- Anderson, "Mitochondrial Dysfunction in Diabetes Mellitus," *Drug Development Research* 46:67-79, 1999. --

Column 35,
Line 25, "$R_2$ is hydroxy, $C_{1-2}$alkly, $C_{1-2}$alkyloxy, halo, -NH2," should read -- $R_2$ is hydroxy, $C_{1-12}$alkyl, $C_{1-12}$alkyloxy, halo, NH$_2$, --.
Line 26, "$C_{7-12}$,aralkyl or heterocycle;" should read -- $C_{7-12}$aralkyl or heterocycle; --.
Line 39, "3 5-difluorophenyl, 3," should read -- 3, 5-difluorophenyl, 3, --.

Signed and Sealed this

Twenty-third Day of April, 2002

Attest:

Attesting Officer

JAMES E. ROGAN
*Director of the United States Patent and Trademark Office*